US012741002B2

(12) United States Patent
Rajendran

(10) Patent No.: US 12,741,002 B2
(45) Date of Patent: Sep. 22, 2026

(54) THERAPEUTIC HERBAL COMPOSITIONS FOR IMPROVING LIVER HEALTH

(71) Applicant: KARALLIEF, INC., Cambridge, MA (US)

(72) Inventor: Krishna Rajendran, Cambridge, MA (US)

( * ) Notice: Subject to any disclaimer, the term of this patent is extended or adjusted under 35 U.S.C. 154(b) by 749 days.

(21) Appl. No.: 18/156,364

(22) Filed: Jan. 18, 2023

(65) Prior Publication Data

US 2023/0226131 A1 Jul. 20, 2023

Related U.S. Application Data

(63) Continuation-in-part of application No. PCT/US2022/042960, filed on Sep. 8, 2022, which is a continuation-in-part of application No. 17/469,566, filed on Sep. 8, 2021, now abandoned.

(51) Int. Cl.

| | |
|---|---|
| ***A61K 36/00*** | (2006.01) |
| ***A61K 36/19*** | (2006.01) |
| ***A61K 36/31*** | (2006.01) |
| ***A61K 36/42*** | (2006.01) |
| ***A61K 36/8965*** | (2006.01) |
| ***A61K 36/9068*** | (2006.01) |
| ***A61P 1/16*** | (2006.01) |

(52) U.S. Cl.

CPC .............. *A61K 36/19* (2013.01); *A61K 36/31* (2013.01); *A61K 36/42* (2013.01); *A61K 36/8965* (2013.01); *A61K 36/9068* (2013.01); *A61P 1/16* (2018.01); *A61K 2236/15* (2013.01); *A61K 2236/331* (2013.01); *A61K 2236/333* (2013.01); *A61K 2236/51* (2013.01)

(58) Field of Classification Search

CPC ........................................................ A61P 1/16

See application file for complete search history.

(56) References Cited

U.S. PATENT DOCUMENTS

| | | | |
|---|---|---|---|
| 2013/0122119 | A1 | 5/2013 | Ghosal et al. |
| 2014/0363526 | A1 | 12/2014 | Chitre et al. |
| 2020/0108115 | A1 | 4/2020 | Antony |

FOREIGN PATENT DOCUMENTS

| | | | |
|---|---|---|---|
| WO | 2007093897 | A2 | 8/2007 |
| WO | 2011080721 | A2 | 7/2011 |

OTHER PUBLICATIONS

Choi et al., Abstract “Hepatoprotective Effects of Brassica rapa (Turnip) on d-Galactosamine Induced Liver Injured Rats”, Korean journal of Pharmacognosy, Dec 30, 2026, 31(4), 258-265.—Cited in the International Search Report.

European Patent Office, Patent Application No. 22868082.3, “Communication pursuant to Article 94(3) EPC”, issued May 19, 2026.

Morya et al., “Hepatoprotection By Natural Products: A Recent Update”, Jan. 1, 2020 (Jan. 1, 2020), pp. 3032-3040, XP093045005.—Cited in the International Search Report.

N.Ghosh et al., “Recent advances in herbal medicine for treatment of liver diseases”, Pharmaceutical Biology, Swets and Zeitlinger, Lisse, NL, vol. 49, No. 9, Sep. 1, 2011 (Sep. 1, 2011), pp. 970-988, XP009155608.

*Primary Examiner* — Qiuwen Mi

(74) *Attorney, Agent, or Firm* — Stonebridge IP, PLLC

(57) ABSTRACT

Compositions including herbal extracts, such as an *Andrographis paniculata* extract, a *Zingiber officinale* (ginger) extract, a *Momordica charantia* extract, a *Brassica rapa* (turnip) extract, an *Asparagus racemosus* extract, and a *Phyllanthus niruri* extract, and methods using such compositions are disclosed. For example, compositions and methods may be used to support, maintain, or improve liver health.

27 Claims, 12 Drawing Sheets

UV 366nm

After Spraying Vanillin Sulphuric Acid (White Light)

A- Composition A Working Standard [KLF/WS/01]

B- Andrographis paniculata Extract Working Standard [AND/WS/18]

C- Composition A [KLF/20001]

After Spraying Vanillin Sulphuric Acid (White Light):

A- Composition A Working Standard [KLF/WS/01]

B- Zingiber officinale Extract Working Standard [GDE/WS/17]

C- Composition A [KLF/20001]

After Spraying Natural Product Reagent [UV366 nm]

A- Composition A Working Standard [KLF/WS/01]

B- Brassica rapa Extract Working Standard [TURP/WS/15]

C- Composition A [KLF/20001]

After Spraying Anisaldehyde sulphuricacid reagent [White Light]

A- Composition A Working Standard [KLF/WS/01]

B- Momordica charantia Extract Working Standard [MCE/WS/17]

C- Composition A [KLF/20001]

After Spraying Vanillin Sulphuric Acid

UV 366nm

(White Light)

A- Composition A Working Standard [KLF/WS/01]

B- Asparagus racemosus Extract Working Standard [ARE/WS/17]

C- Composition A [KLF/20001]

After Spraying Natural Product Reagent [UV 366nm]

After Spraying Natural Product Reagent + PEG [UV366 nm]

A- Composition A Working Standard [KLF/WS/01]

B- Phyllanthus niruri Extract Working Standard [PHY/WS/16]

C- Composition A [KLF/20001]

THERAPEUTIC HERBAL COMPOSITIONS FOR IMPROVING LIVER HEALTH

RELATED APPLICATIONS

This application claims priority to and is a continuation-in-part of PCT/US2022/042960, filed Sep. 8, 2022, which is a continuation-in-part of U.S. patent application Ser. No. 17/469,566, filed Sep. 8, 2021, all entitled "THERAPEUTIC HERBAL COMPOSITIONS FOR IMPROVING LIVER HEALTH," and all of which are hereby incorporated by reference in their entirety.

BACKGROUND

The present disclosure relates generally to herbal compositions, dosage forms comprising such compositions, pharmaceutical kits comprising an effective dosage of such compositions, methods of supporting, maintaining, or improving liver health by administering such compositions, and methods for producing such compositions.

The liver is a critical organ of the human body and plays a key role in metabolism and excretion. The liver performs many essential functions, including the synthesis of cholesterol, triglycerides, proteins, blood-clotting factors, glycogen, and bile. Symptoms of liver disorders can include jaundice, swelling, abdominal pain, confusion, bleeding, fatigue, weakness, nausea, vomiting, and weight loss. Alcohol can be toxic to the liver, especially in high doses. Long-term alcohol abuse is a common cause of liver disorders.

Modern drugs do not provide many effective options for treating liver disorders. The existing liver medications may also cause side effects that can exacerbate the liver condition. Thus, there is a need for safe alternative approaches to support, maintain, or improve liver health.

BRIEF SUMMARY OF THE DISCLOSURE

The present disclosure addresses these needs by providing herbal compositions useful for supporting, maintaining, or improving liver health, dosage forms comprising the herbal compositions, pharmaceutical kits comprising an effective dosage of such compositions, methods of administering the herbal compositions, and methods of making the herbal compositions.

In one aspect, the present disclosure is directed to an herbal composition comprising an *Andrographis paniculata* extract, a *Zingiber officinale* (ginger) extract, and a *Brassica rapa* (turnip) extract. In some embodiments, the herbal composition further comprises a *Momordica charantia* extract, an *Asparagus racemosus* extract, a *Phyllanthus niruri* extract, or any combination thereof.

In some embodiments, the herbal composition comprises from about 15% to about 70% of the *Andrographis paniculata* extract, from about 5% to about 45% of the *Zingiber officinale* (ginger) extract, and from about 5% to about 45% of the *Brassica rapa* (turnip) extract, by weight relative to the total weight of the composition. In some embodiments, the herbal composition further comprises from about 25% to about 35% of the *Momordica charantia* extract, from about 10% to about 20% of the *Asparagus racemosus* extract, and/or from about 10% to about 20% of the *Phyllanthus niruri* extract, by weight relative to the total weight of the composition.

In another aspect, the composition further comprises at least one pharmaceutically acceptable excipient or antioxidant. In some embodiments, the composition is a dietary supplement. In some embodiments, the dosage form is a dosage form for oral administration. In some embodiments, the dosage form is a powder. In some embodiments, the powder can be used in a food or beverage product. In some embodiments, the composition can be used in an oil form in personal care products. In some embodiments, the dosage form is a capsule. In some embodiments, the capsule is a gelatin capsule, a polysaccharide capsule, or a vegetarian capsule. In some embodiments, the dosage form for oral administration comprises at least one pharmaceutically acceptable excipient.

In another aspect, the present disclosure is directed to a dosage form for oral administration comprising an herbal composition according to the present disclosure. The herbal composition may be any of the herbal compositions according to the present disclosure. In some embodiments, the dosage form for oral administration comprises from about 0.1 g to about 1.0 g of an herbal composition of the present disclosure. For example, in some embodiments, the dosage form for oral administration comprises about 0.5 g of an herbal composition of the present disclosure.

In another aspect, the present disclosure is directed to a method of supporting, maintaining, or improving liver health in a subject, comprising administering an effective amount of an herbal composition of the present disclosure to the subject. The herbal composition may be any herbal composition according to the present disclosure. In some embodiments, the subject is a mammal. In some embodiments, the subject is a human.

In some embodiments, the herbal composition of the present disclosure is administered orally. In some embodiments, the oral daily dosage of the herbal composition ranges from about 0.1 g to about 4.0 g. For example, in some embodiments, the daily dosage is about 1.0 g per day orally. In some embodiments, the herbal composition is administered twice per day orally. For example, in some embodiments, about 0.5 g of the herbal composition is administered orally twice per day, for a total daily dosage of about 1.0 g per day.

In another aspect, the present disclosure is directed to a method of making an herbal composition comprising: extracting *Andrographis paniculata* aerial parts to form an *Andrographis paniculata* extract, extracting *Zingiber officinale* (ginger) rhizomes to form a *Zingiber officinale* (ginger) extract, extracting *Momordica charantia* fruits to form a *Momordica charantia* extract, extracting *Brassica rapa* (turnip) to form a *Brassica rapa* (turnip) extract, extracting *Asparagus racemosus* roots to form an *Asparagus racemosus* extract, and extracting *Phyllanthus niruri* aerial parts to form a *Phyllanthus niruri* extract; combining the *Andrographis paniculata* extract, the *Zingiber officinale* (ginger) extract, the *Momordica charantia* extract, the *Brassica rapa* (turnip) extract, the *Asparagus racemosus* extract, and the *Phyllanthus niruri* extract; and blending the combined extracts.

DETAILED DESCRIPTION OF THE DISCLOSURE

Figure 1:
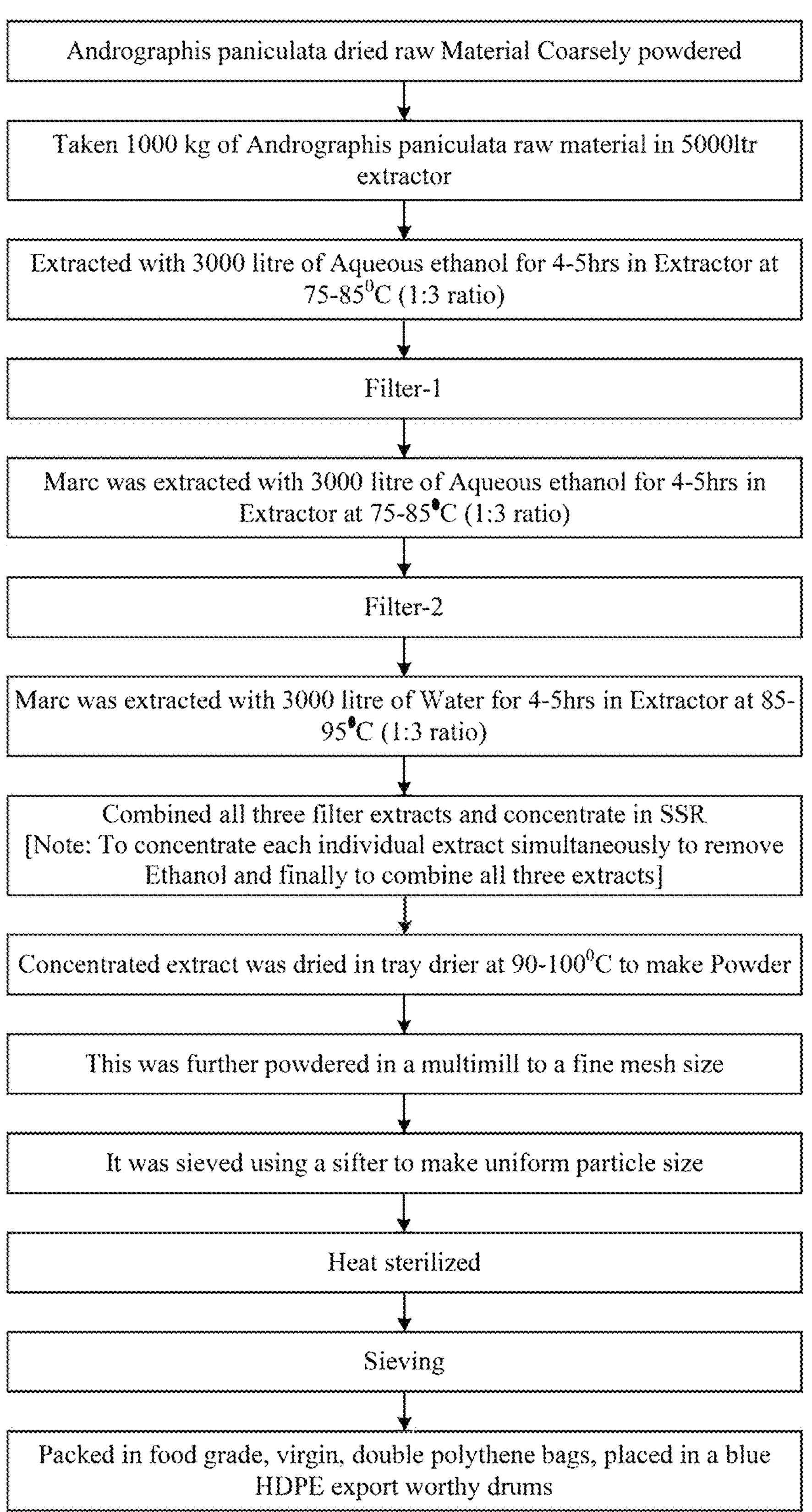
FIG. 1 illustrates an exemplary process for producing an *Andrographis paniculata* extract according to the present disclosure.

Particular aspects of the disclosure are described in greater detail below. The terms and definitions as used in the present application and as clarified herein are intended to represent the meaning within the present disclosure. The patent and scientific literature referred to herein and referenced above is hereby incorporated by reference. The terms and definitions provided herein control, if in conflict with terms and/or definitions incorporated by reference.

As used herein, "a" or "an" entity refers to one or more of that entity. As such, the terms "a" (or "an"), "one or more," and "at least one" are used interchangeably herein.

As used herein, the term "about" refers to including a 10%, 5%, or 3% difference of a numerical value that comes after the term "about."

As used herein, the term "reduce" indicates a lessening or decrease of an indicated value relative to a reference value. In some embodiments, the term "reduce" (including "reduction") refers to a lessening or a decrease of an indicated value by about 5%, 10%, 15%, 20%, 25%, 30%, 35%, 40%, 45%, or 50% relative to a reference value. Unless indicated otherwise, the percentage (%) of ingredients refers to the total % by weight typically on a dry weight basis unless otherwise indicated.

As used herein, the term "concentrating" refers to an operation that aims to increase the concentration of the desired component, especially by removing extraction solvent. The term also encompasses the operation of drying an extract so as to remove all or almost all of the aqueous solvent (and endogenous water) contained therein.

As used herein, the terms "enriched" and/or "enriching" mean that a higher amount of a desired component, such as one or more active ingredients, is included in an herbal composition, rather than the herb in natural form.

As used herein, the terms "a subject in need of treatment therefor" and/or "a subject in need thereof" as used herein mean a subject who wants or needs to support, maintain, or improve liver health using an herbal composition described herein.

As used herein, the term "administering" means giving an herbal composition disclosed herein to a subject by another person, such as a health professional, or by self-administration by the subject.

As used herein, the term "livolides" refers to certain active compounds in *Andrographis paniculata* that provide pharmacological activity or other direct effect in the support, maintenance or improvement of liver health.

As used here, the term "zinzirols" refers to certain active compounds in *Zingiber officinale* that provide pharmacological activity or other direct effect in the support, maintenance or improvement of liver health.

As used herein, the term "turnitrates" refers to active compounds in *Brassica rapa* that provide pharmacological activity or other direct effect in the support, maintenance or improvement of liver health.

As used herein, the term "saponins" refers to certain active compounds in *Asparagus racemosus* that provide pharmacological activity or other direct effect in the support, maintenance or improvement of liver health.

As used herein, the term "tannins" refers to certain active compounds in *Phyllanthus niruri* that provide pharmacological activity or other direct effect in the support, maintenance or improvement of liver health.

As used herein, the term "bitters" refers to certain active compounds in *Momordica charantia* that provide pharmacological activity or other direct effect in the support, maintenance or improvement of liver health.

The present disclosure is directed to herbal compositions comprising at least one herbal extract. The present disclosure is also directed to dosage forms comprising herbal compositions. The present disclosure is also directed to methods of supporting, maintaining, or improving liver health. The present disclosure is also directed to methods of making herbal compositions.

The herbal compositions of the present disclosure comprise at least one herbal extract. In some embodiments, the at least one herbal extract is chosen from an *Andrographis paniculata* extract, a *Zingiber officinale* (ginger) extract, and a *Brassica rapa* (turnip) extract. In some embodiments, the herbal composition further comprises a *Momordica charantia* extract, an *Asparagus racemosus* extract, a *Phyllanthus niruri* extract, or any combination thereof.

In some embodiments of the present disclosure, the herbal composition comprises an *Andrographis paniculata* extract. In some embodiments, the *Andrographis paniculata* extract is an extract of *Andrographis paniculata* aerial parts. In some embodiments, the *Andrographis paniculata* aerial parts comprise *Andrographis paniculata* leaves.

In some embodiments, the *Andrographis paniculata* leaves are dried and powdered before extraction. In some embodiments, the *Andrographis paniculata* is extracted with an extraction solvent chosen from water, alcohol, and combinations thereof. In some embodiments, the extraction solvent is water. In some embodiments, the extraction solvent is an alcohol, such as methanol, ethanol, propanol (such as isopropanol), butanol, or mixtures thereof. In some embodiments, the extraction solvent is an aqueous alcohol solution, such as aqueous ethanol, for example, 40%, 50%, 60%, 70%, or 80% ethanol in water (v/v). In some embodiments, the weight ratio of *Andrographis paniculata* to extraction solvent is about 1:3. In some embodiments, *Andrographis paniculata* is extracted at an elevated temperature, such as, for example, from about 75° C. to about 85° C. *Andrographis paniculata* may be extracted more than once, such as three times, and the extracts may be combined and distilled. The distilled *Andrographis paniculata* extracts may be dried and further powdered to a fine mesh size. The powdered *Andrographis paniculata* extract may be heat sterilized and sieved.

In some embodiments, an *Andrographis paniculata* extract comprises livolides.

Chemical structures and molecular information on Various Livolides in the herbal composition:

Livolides are the Andrographolides, present in the leaves of *Andrographis* paniculate. There are four Livolides, estimated in the herbal composition.

The content of these 4 Livolides in *Andrographis paniculatus* extract is standardised at "Not less than 10%" by HPLC.

The content of these 4 Livolides in the herbal composition is standardised at "Not less than 1.5%" by HPLC. This formula has been tested clinically for management of liver health.

The quality of every batch of *Andrographis paniculatus* extract, manufactured is tested and qualified for use in the herbal composition. Similarly, every batch of the herbal composition is also tested as per specifications and qualified for using in formulated product which is essential for consistent efficacy of the herbal composition.

The chemical structure and molecular information of these 4 livolides are given below:

1. Andrographolide

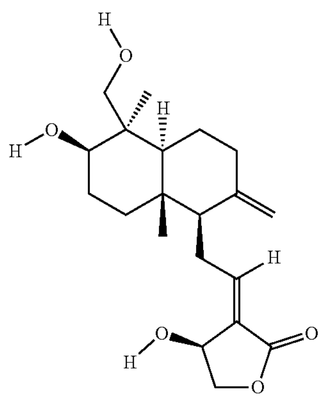 [SMILES: C=C1CC[C@@H]2[C@](C)(CO)[C@H](O)CC[C@@]2(C)[C@@H]1C/C=C1/C(=O)OC[C@H]1O]

Chemical names: ent-(3β,12E,14R)-3,14,19-Trihydroxy-8(17),12-labdadien-16,15-olide, *Andrographis*, (3E,4S)-3-[2-[(1R,4aS,5R,6R,8aS)-Decahydro-6-hydroxy-5-(hydroxymethyl)-5,8a-dimethyl-2-methylene-1-naphthalenyl] ethylidene]dihydro-4-hydroxy-2(3H)-furanone Molecular Weight: 350.45

2. Neoandrographolide

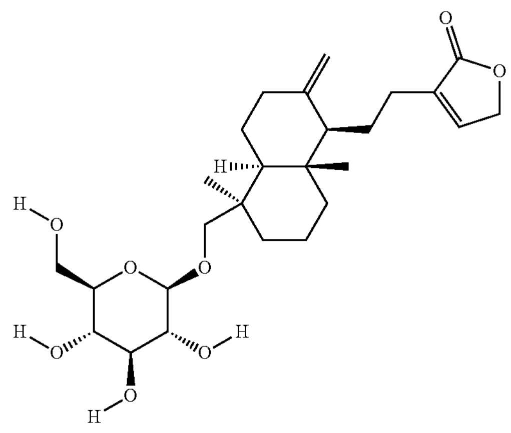 [SMILES: C=C1CC[C@@H]2[C@](C)(CO[C@@H]3O[C@H](CO)[C@@H](O)[C@H](O)[C@H]3O)CCC[C@@]2(C)[C@@H]1CCC1=CCOC1=O]

Chemical names: ent-19-Hydroxy-8(17),13-labdadien-16,15-olide 19-O-β-D-glucopyranoside, D-Glucopyranosyloxy)methyl]decahydro-5,8a-dimethyl-2-methylene-1-naphthalenyl]ethyl]-2(5H)-furanone Molecular Weight: 480.59

3. 14-deoxy-11, 12-didehydrographolide

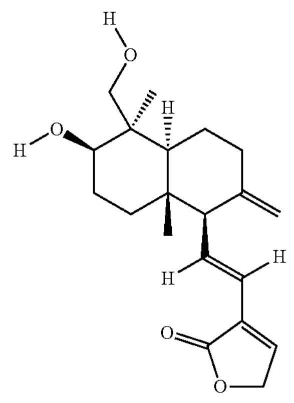 [SMILES: C=C1CC[C@@H]2[C@](C)(CO)[C@H](O)CC[C@@]2(C)[C@@H]1/C=C/C1=CCOC1=O]

Chemical names: 3-[(1E)-2-[(1R,4aS,5R,6R,8aR)-Decahydro-6-hydroxy-5-(hydroxymethyl)-5,8a-dimethyl-2-methylene-1-naphthalenyl]ethenyl]-2(5H)-furanone, ent-(3β,11E)-3,19-Dihydroxy-8(17),11,13-labdatrien-16,15-olide Molecular weight: 332.43

4. Andrograpanin

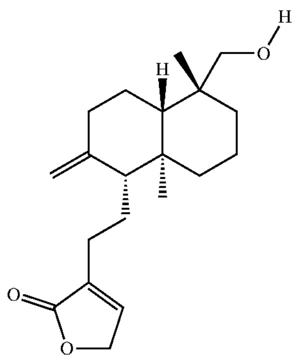 [SMILES: C=C1CC[C@@H]2[C@](C)(CO)CCC[C@@]2(C)[C@@H]1CCC1=CCOC1=O]

Chemical names: 3,14-Dideoxyandrographolide, ent-19-Hydroxy-8(17),13-labdadien-16,15-olide, 3-[2-[(1R,4aS, 5R,8aS)-Decahydro-5-(hydroxymethyl)-5,8a-dimethyl-2-methylene-1-naphthalenyl]ethyl]-2(5H)-furanone.

Molecular weight: 318.45

The content of livolides can be estimated by using a high pressure liquid chromatography (HPLC) method, for example, the Shimadzu LC-20AD Prominence Gradient system. HPLC column may be Phenomenex C-18, Luna, -SS column 250.0×4.6 mm, 5.0 micron particle size. Mobile phase may be a gradient system of [A] 0.14 g/L of potassium dihydrogen orthophosphate and [B] acetonitrile. Detection may be at 223.0 nm and the flow rate may be 1.5 mL/min.

Assay of livolides can be calculated as follows:

$$\frac{\text{Standard weight}}{\text{Sample weight}} \times \frac{\text{Sample area}}{\text{Standard area.}} \times \% \text{ of Standard assay} = \% \text{ of } \textit{Livolides} \text{ in Sample}$$

Following is an exemplary HPLC test.

Standard Solution Preparation: 100.0 mg of *Andrographis paniculata* extract working standard (prepared using botanically authenticated *Andrographis paniculata* herb) and 25.0 ml of methanol are added in a 50.0 ml volumetric flask. The solution is sonicated in a sonicator for 5-10 minutes and heated in a water bath for 15-20 minutes at 60-70° C. The solution is cooled in room temperature. The solution is transferred to a 50.0 ml standard flask and the volume is made up to 50.0 ml with acetonitrile. The solution is filtered and transferred to an LC auto sampler vial.

Sample Solution Preparation: 200.0 mg of an herbal composition and 25.0 ml of methanol are added in a 50.0 ml volumetric flask. The solution is sonicated in a sonicator for 5-10 minutes and heated in a water bath for 15-20 minutes at 60-70° C. The solution is cooled in room temperature. The solution is transferred to a 50.0 ml standard flask and the volume is made up to 50.0 ml with acetonitrile. The solution is filtered and transferred to an LC auto sampler vial.

Figure 9:
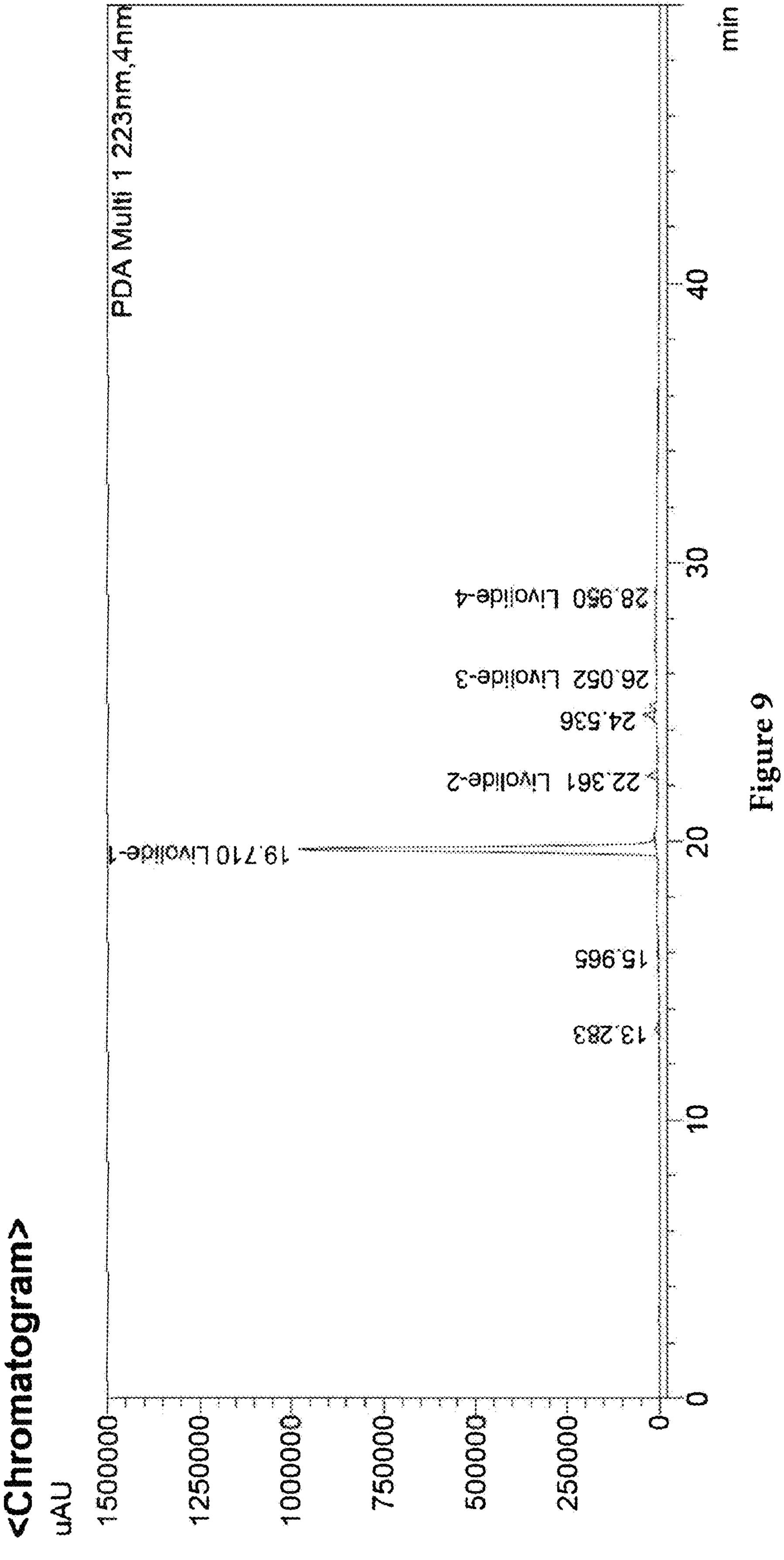
FIG. 9 is a chromatogram of livolides in a working standard preparation of an herbal composition.
Figure 10:
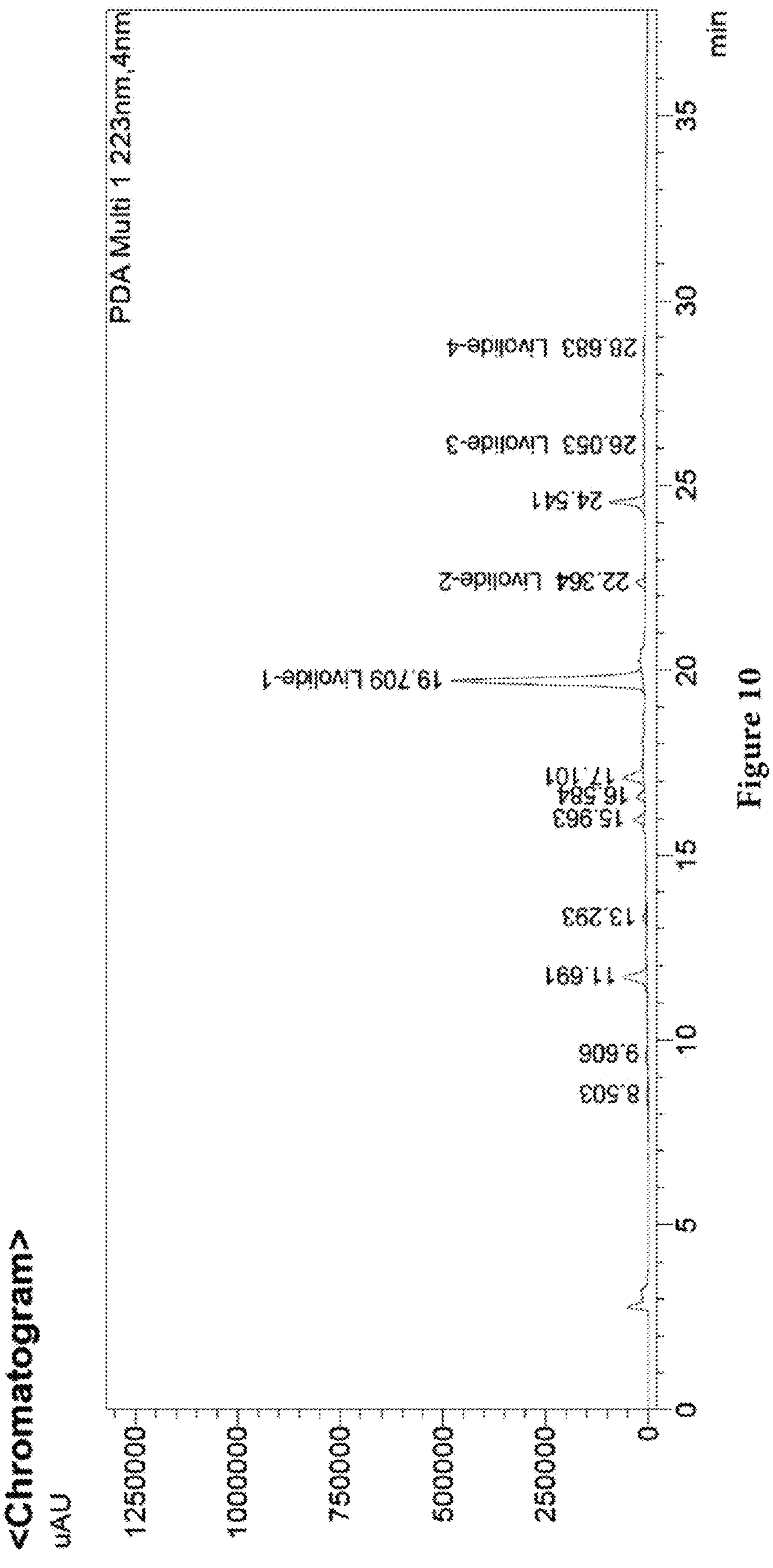
FIG. 10 is a chromatogram of livolides in a sample preparation of an herbal composition for comparison with the chromatogram in FIG. 9.

For example, HPLC analysis of total Livolides in the herbal composition:

Introduction: The HPLC analysis of a typical batch of the herbal composition (KLF/21003) is given below covering the method of analysis, calculations, and chromatograms in FIGS. 9 and 10.

HPLC instrument: Shimadzu LC-20AD Prominence Gradient system

HPLC Column: Phenomenex C-18, Luna, -SS column 250×4.6 mm, 5 micron particle size.

Mobile phase: [A] 0.14 g of potassium dihydrogen phosphate in 900 ml of water, add 0.5 ml of phosphoric acid, dilute with water to 1000 ml.

[B] Acetonitrile [Gradient System]

Detection: 223 nm

Flow rate: 1.5 mL/min

Gradient System

| TIME (min) | B CONCENTRATION (%) |
|---|---|
| 0.01 | 5 |
| 18 | 45 |
| 25 | 80 |
| 28 | 80 |
| 35 | 45 |
| 40 | 5 |
| 45 | 5 |

Working standard preparation: Weigh accurately about 25 mg of Livolides working standard [Batch No: AND/WS/17] and extract in 25 ml of Methanol in 50 ml volumetric flask. Mix well, Sonicate the solution in a sonicator for 5-10 minutes in room temperature. Heat the solution on water bath for 15-20 min at 60°-70° C. Cool the solution at room temperature, transfer it to a 50 ml standard flask and make up the volume to 50 ml with Acetonitrile, Filter and inject the solution.

Sample preparation: Weigh accurately about 500 mg of the herbal composition extract sample [Batch No: KLF/21003] and extract in 25 ml of Methanol in 50 ml volumetric flask. Mix well, Sonicate the solution in a sonicator for 5-10 minutes in room temperature. Heat the solution on water bath for 15-20 min at 60°-70° C. Cool the solution at room temperature, transfer it to a 50 ml standard flask and make up the volume to 50 ml with Acetonitrile, Filter and inject the solution.

Inject 20 ul of working standard and sample solutions separately. The approximate relative retention times of the four Livolides are provided in the following table mentioned below.

| Analyte | Approximate Relative Retention time |
|---|---|
| Livolide -1 | 1.0 |
| Livolide -2 | 1.1 |
| Livolide -3 | 1.3 |
| Livolide -4 | 1.4 |

Calculate the Peak areas of the four Livolides in the standard as compared to sample and calculate the assay of total Livolides in the sample.

Calculation of Assay of Total Livolides:

$$\frac{\textit{Std} \text{ weight}}{\text{Sample weight}} \times \frac{\text{Sample area}}{\text{Standard area}} \times \% \text{ of Standard assay} = \% \text{ of total } \textit{Livolides} \text{ in Sample}$$

Livolides Calculation [Batch No: KLF/21003]:

Standard Batch No: AND/WS/17

Standard Purity 76.2% of all four Livolides

Standard Weight 26.3 mg in 25 ml of Methanol and 25 ml of Acetonitrile

Standard Area 12367027

Sample batch No KLF/21003

Sample Weight 500.39 mg in 25 ml of Methanol and 25 ml of Acetonitrile

Sample Area 6175842

Calculation:

$$(26.3/500.39)\times(6175842/12367027)\times 76.2\%=2.0\% \text{ of Total Livolides.}$$

In some embodiments, an herbal composition comprises enriched amounts of livolides. For example, the herbal composition may comprise no less than 0.5%, no less than 0.6%, no less than 0.7%, no less than 0.8%, no less than 0.9%, no less than 1.0%, no less than 1.1%, no less than 1.2%, no less than 1.3%, no less than 1.4%, no less than 1.5%, no less than 1.6%, no less than 1.7%, no less than 1.8%, no less than 1.9%, or no less than 2.0% of livolides in the composition, by weight relative to the total weight of the composition. In one embodiment, the herbal composition comprises no less than 1.5% of livolides in the composition.

In some embodiments, an herbal composition comprises from about 1.0% to about 5.0% of livolides, by weight relative to the total weight of the herbal composition. For example, an herbal composition may comprise from about 1.0% to about 5.0%, from about 1.0% to about 4.0%, from about 1.0% to about 3.0%, or from about 1.0% to about 2.0% of livolides, by weight relative to the total weight of the herbal composition.

In some embodiments, an herbal composition comprises from about 10% to about 50% of an *Andrographis paniculata* extract, by weight relative to the total weight of the herbal composition, such as from about 10% to about 40%, from about 20% to about 40%, from about 15% to about 30%, from about 15% to about 25%, from about 18% to about 22%, or from about 19% to about 21% of the *Andrographis paniculata* extract, by weight relative to the total weight of the herbal composition.

In some embodiments of the present disclosure, the herbal composition comprises a *Zingiber officinale* (ginger) extract. In some embodiments, the *Zingiber officinale* (ginger) extract is an extract of *Zingiber officinale* (ginger) root parts. In some embodiments, the *Zingiber officinale* (ginger) extract is an extract of *Zingiber officinale* (ginger) rhizomes.

In some embodiments, the ginger rhizomes are dried and powdered before extraction. In some embodiments, the ginger rhizomes are extracted with an extraction solvent chosen from water, alcohol, and combinations thereof. In some embodiments, the extraction solvent is water. In some embodiments, the extraction solvent is an alcohol, such as methanol, ethanol, propanol (such as isopropanol), butanol, or mixtures thereof. In some embodiments, the extraction solvent is an aqueous alcohol solution, such as aqueous ethanol, for example, 40%, 50%, 60%, 70%, or 80% ethanol in water (v/v). In some embodiments, the weight ratio of *Zingiber officinale* (ginger) to extraction solvent is about 1:3. In some embodiments, the ginger is extracted at an elevated temperature, such as, for example, from about 75° C. to about 85° C. The *Zingiber officinale* (ginger) may be extracted more than once, such as three times, and the extracts may be combined and distilled. The distilled *Zingiber officinale* (ginger) extracts may be dried and further powdered to a fine mesh size. The powdered *Zingiber officinale* (ginger) extracts may be heat sterilized and sieved.

In some embodiments, the *Zingiber officinale* (ginger) extract comprises zinzirols. The herbal composition comprises four zinzirols.

Zinzirol-1 has the compound name (6)-gingerol, the chemical formula $C_{17}H_{26}O_4$, and the IUPAC name (5S)-5-hydroxy-1-(4-hydroxy-3-methoxyphenyl)decan-3-one.

Zinzirol-2 has the compound name (8)-gingerol, the chemical formula $C_{19}H_{30}O_4$, and the IUPAC name 5-hydroxy-1-(4-hydroxy-3-methoxyphenyl)-3-dodecanone.

Zinzirol-3 has the compound name (6)-shagaol, the chemical formula $C_{17}H_{24}O_3$, and the IUPAC name (4E)-1-(4-hydroxy-3-methoxyphenyl)dec en-3-one.

Zinzirol-4 has the compound name (10)-gingerol, the chemical formula $C_{21}H_{34}O_4$, and the IUPAC name (5S)-hydroxy-1-(4-hydroxy-3-methoxyphenyl)-3-tetradecanone.

The content of zinzirols can be estimated by using a high pressure liquid chromatography (HPLC) method, for example, the Shimadzu LC-20AD Prominence Gradient system. HPLC column may be Phenomenex C-18, Luna, -SS column 250.0×4.6 mm, 5.0 micron particle size. Mobile phase may be acetonitrile: 0.1% phosphoric acid:methanol [55:44:1]. Detection may be at 282.0 nm and the flow rate may be 1.0 mL/min.

Assay of zinzirols can be calculated as follows:

$$\frac{\text{Standard weight}}{\text{Sample weight}} \times \frac{\text{Sample area}}{\text{Standard area}} \times \% \text{ of Standard assay} = \% \text{ of } \textit{Zinzirols} \text{ in Sample}$$

Following is an exemplary HPLC test.

Standard Solution Preparation: 100.0 mg of *Zingiber officinale* (ginger) extract working standard (prepared using botanically authenticated ginger) and 25.0 ml of methanol are added in a 50.0 ml volumetric flask. The solution is sonicated in a sonicator for 5-10 minutes and heated in a water bath for 15-20 minutes at 70-80° C. The solution is cooled in room temperature. The solution is transferred to a 25.0 ml standard flask and made up to a volume of 25.0 ml with methanol. The solution is filtered and transferred to an LC auto sampler vial.

Sample Solution Preparation: 200.0 mg of an herbal composition and 25.0 ml of methanol are added in a 50.0 ml volumetric flask. The solution is sonicated in a sonicator for 5-10 minutes and heated in a water bath for 15-20 minutes at 60-70° C. The solution is cooled in room temperature. The solution is transferred to a 25.0 ml standard flask and made up to a volume of 25.0 ml with methanol. The solution is filtered and transferred to an LC auto sampler vial.

Figure 11:
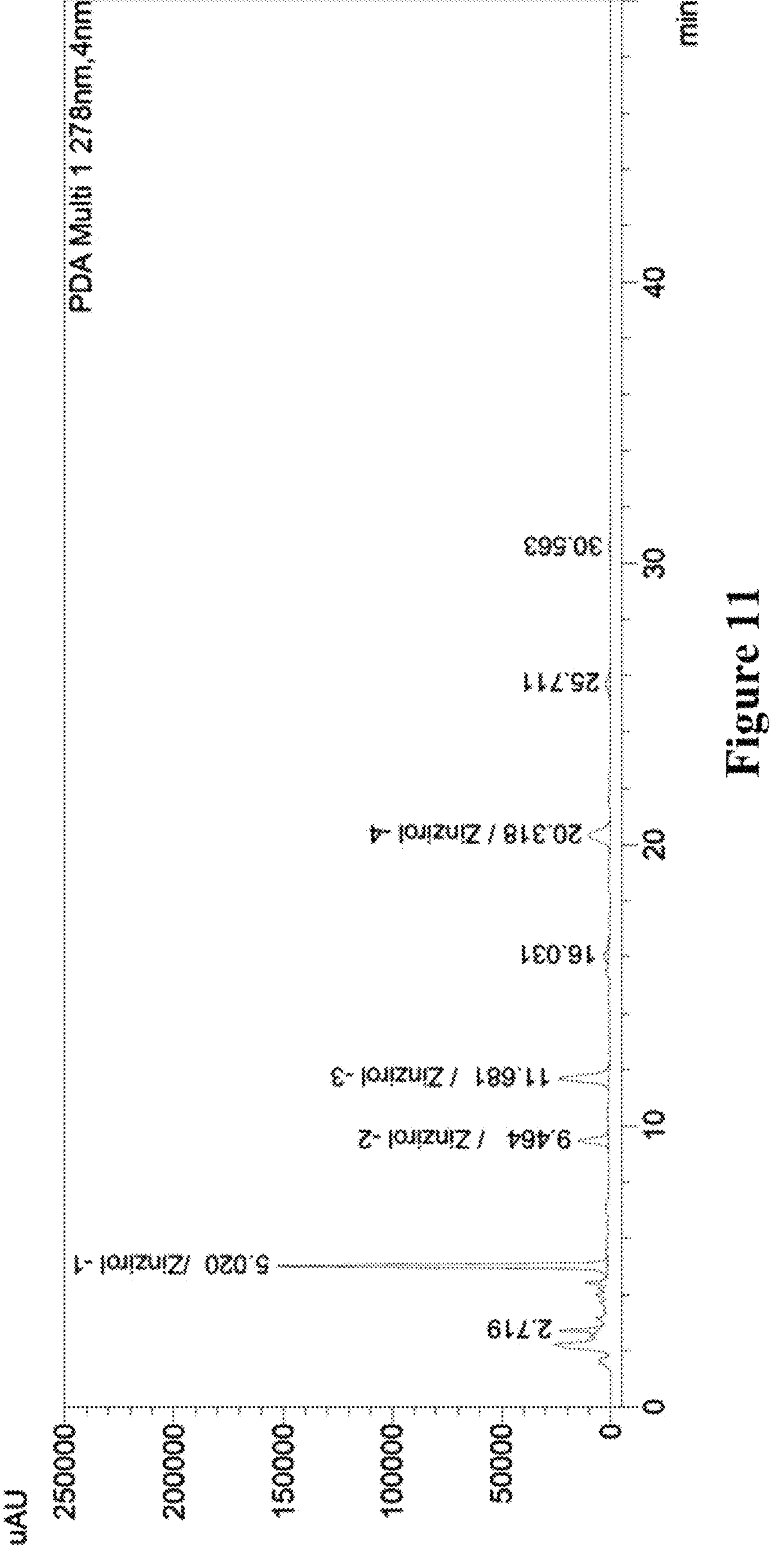
FIG. 11 is a chromatogram of zinzirols in a working standard preparation of an herbal composition.
Figure 12:
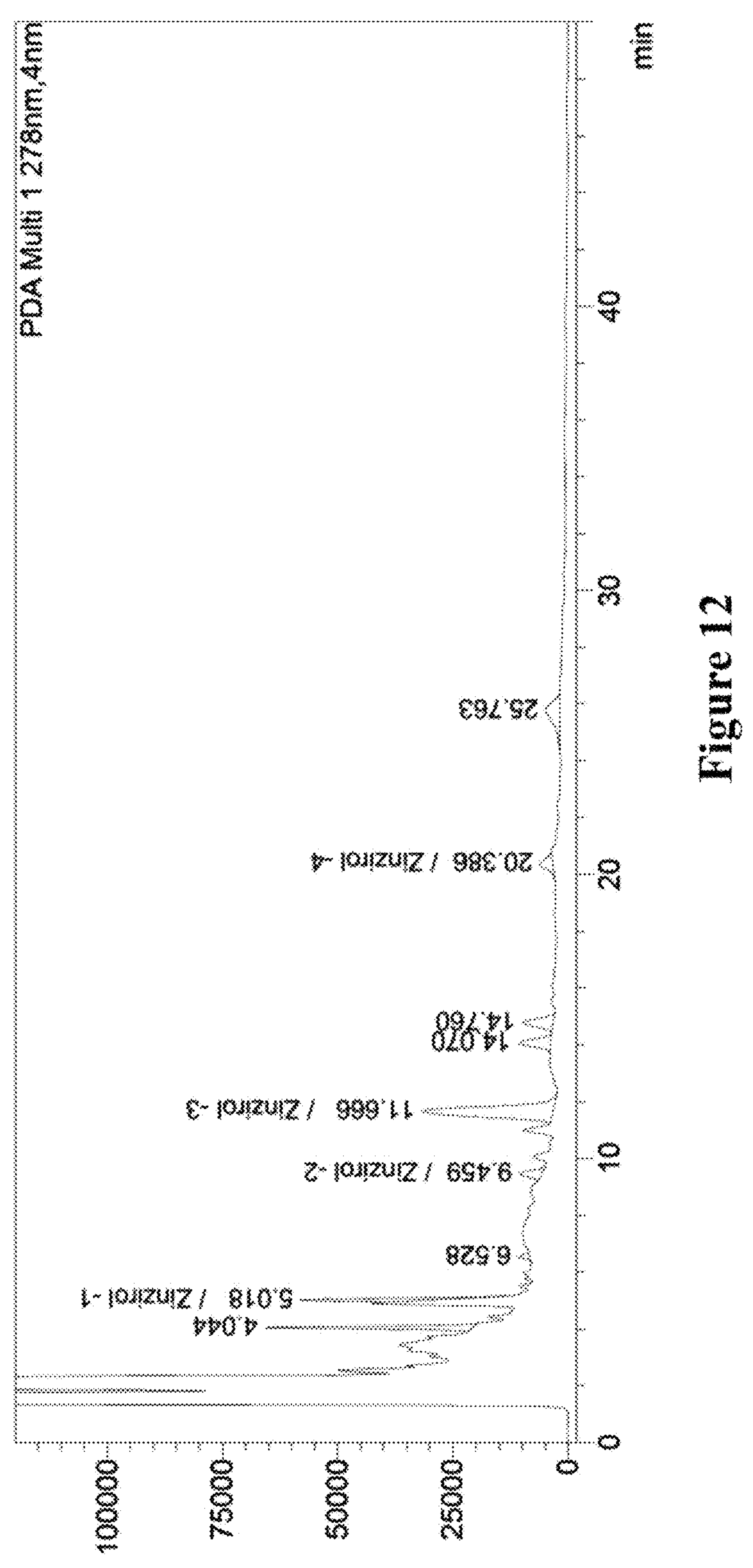
FIG. 12 is a chromatogram of zinzirols in a sample preparation of an herbal composition for comparison with the chromatogram in FIG. 11.

For example, HPLC analysis of total Zinzirols In the herbal composition:

Introduction: The HPLC analysis of a typical batch of the herbal composition (KLF/21003) is given below covering the method of analysis, calculations and chromatograms in FIGS. 11 and 12.

HPLC instrument: Shimadzu LC-20AD Prominence Gradient system

HPLC Column: Phenomenex C-18, Luna, -SS column 250×4.6 mm, 5 micron particle size.

Mobile phase: [A] Water and (B) Acetonitrile [45:55]

Detection: 278 nm

Flow rate: 1.3 ml/min

Working standard preparation: Weigh accurately about 100 mg of Zinzirols extract working standard [Batch No: GDE/WS/17] and extract in 25 ml of Methanol in 50 ml volumetric flask. Mix well, Sonicate the solution in a sonicator for 5-10 minutes in room temperature. Heat the solution on water bath for 15-20 min at 60°-70° C. Cool the solution at room temperature, transfer it to a 25 ml standard flask and make up the volume to 25 ml with methanol, Filter and inject the solution.

Sample preparation: Weigh accurately about 500 mg of the herbal composition extract sample [Batch No: KLF/21003] and extract in 25 ml of Methanol in 50 ml volumetric flask. Mix well, Sonicate the solution in a sonicator for 5-10 minutes in room temperature. Heat the solution on water bath for 15-20 min at 60°-70° C. Cool the solution at room temperature, transfer it to a 25 ml standard flask and make up the volume to 25 ml with methanol. Filter and inject the solution.

Inject 20 ul of working standard and sample solutions separately. The approximate relative retention times of the different Zinzirols are provided in the following table mentioned below

| Analyte | Approximate Relative Retention time |
|---|---|
| Zinzirol 1 | 1.0 |
| Zinzirol 2 | 1.8 |
| Zinzirol 3 | 2.3 |
| Zinzirol 4 | 4.0 |

Calculate the Peak areas of the four Zinzirols in the standard as compared to sample and calculate the assay of Total Zinzirols in the sample.

Calculation of Assay of Total Zinzirols:

$$\frac{\textit{Std} \text{ weight}}{\text{Sample weight}} \times \frac{\text{Sample area}}{\text{Standard area}} \times \% \text{ of Standard assay} = \% \text{ of Total } \textit{Zinzirols} \text{ in Sample}$$

Zinzirols Calculation [Batch No:KLF/21003]:

Standard Batch No GDE/WS/17

Standard Purity 5.3% of all four Zinzirols

Standard Weight 104.89 mg in 25 ml of Methanol

Standard Area 2109650

Sample batch No KLF/21003

Sample Weight 500.17 mg in 25 ml of Methanol Sample Area 987012

Calculation:

(104.89/500.17)×(987012/2109650)×5.3%=0.52% of Total Zinzirols content.

In some embodiments, an herbal composition comprises enriched amounts of zinzirols. For example, the herbal composition may comprise no less than 0.2%, no less than 0.3%, no less than 0.4%, no less than 0.5%, no less than 0.6%, no less than 0.7%, no less than 0.8%, no less than 0.9%, no less than 1.0%, no less than 1.1%, no less than 1.2%, no less than 1.3%, no less than 1.4%, no less than 1.5%, no less than 1.6%, no less than 1.7%, no less than 1.8%, no less than 1.9%, or no less than 2.0% of zinzirols in the composition, by weight relative to the total weight of the composition. In one embodiment, the herbal composition comprises no less than 0.4% of zinzirols in the composition.

In some embodiments, an herbal composition comprises from about 0.2% to about 3.0% of zinzirols, by weight relative to the total weight of the herbal composition. For example, an herbal composition may comprise from about 0.2% to about 2.5%, from about 0.2% to about 2.0%, from about 0.2% to about 1.0%, or from about 0.2% to about 0.6% of zinzirols, by weight relative to the total weight of the herbal composition.

In some embodiments, an herbal composition comprises from about 5% to about 30% of the *Zingiber officinale* (ginger) extract, such as from about 5% to about 20%, from about 5% to about 15%, from about 10% to about 15%, from about 8% to about 13%, from about 9% to about 11%, from about 18% to about 22%, or from about 19% to about 21% of the *Zingiber officinale* (ginger) extract, by weight relative to the total weight of the herbal composition.

In some embodiments of the present disclosure, the herbal composition comprises a *Brassica rapa* (turnip) extract. In some embodiments, the *Brassica rapa* (turnip) extract is an extract of *Brassica rapa* (turnip) roots. In some embodiments, the *Brassica rapa* (turnip) extract is an extract of turnip roots.

In some embodiments, *Brassica rapa* (turnip) roots are dried and powdered before extraction. In some embodiments, the *Brassica rapa* (turnip) is extracted with an extraction solvent chosen from water, alcohol, and combinations thereof. In some embodiments, the extraction solvent is water. In some embodiments, the extraction solvent is an alcohol, such as methanol, ethanol, propanol (such as isopropanol), butanol, or mixtures thereof. In some embodiments, the extraction solvent is an aqueous alcohol solution, such as aqueous ethanol, for example, 40%, 50%, 60%, 70%, or 80% ethanol in water (v/v). In some embodiments, the weight ratio of *Brassica rapa* (turnip) to extraction solvent is about 1:3. In some embodiments, the *Brassica rapa* (turnip) is extracted at an elevated temperature, such as, for example, from about 75° C. to about 85° C. The *Brassica rapa* (turnip) may be extracted more than once, such as three times, and the extracts may be combined and distilled. The distilled *Brassica rapa* (turnip) extracts may be dried and further powdered to a fine mesh size. The powdered *Brassica rapa* (turnip) extracts may be heat sterilized and sieved.

In some embodiments, the *Brassica rapa* (turnip) extract comprises turnitrates. Turnitrates comprise a polyatomic ion of the formula $NO_3$. Salts containing the polyatomic ion are called nitrates. The *Brassica rapa* extract may comprise many phytocompounds as turnitrates having the nitrate ion.

The content of turnitrates can be estimated by using an ultraviolet (UV) spectrophotometer method.

Assay of turnitrates can be calculated as follows:

$$\frac{\text{Standard weight}}{\text{Sample weight}} \times \frac{\text{Sample Absorbance}}{\text{Standard Absorbance}} \times \% \text{ of Standard assay} = \% \text{ of } \textit{Turnitrates} \text{ in Sample}$$

The UV method may require reagents, including salicylic acid, sodium hydroxide, distilled water, and concentrated sulphuric acid.

Following is an exemplary UV test.

Salicylic Acid—Sulphuric Acid Reagent: 5.0 g of salicylic acid is dissolved in 100.0 ml of concentrated sulphuric acid in a 200.0 ml beaker. It is mixed slowly and transferred to a brown bottle with a lid.

2 N Sodium Hydroxide [NaOH]: 40.0 g of sodium hydroxide pellets are added in a 500.0 ml beaker. 100.0 ml of distilled water is added. The solution is sonicated in a sonicator for 5-10 minutes. The solution is transferred to a 500.0 ml volumetric flask. The total volume of 500.0 ml is made up with distilled water.

Standard Solution Preparation: 200.0 mg of *Brassica rapa* (turnip) extract working standard (prepared using botanically authenticated *Brassica rapa* (turnip) roots and 25.0 ml of water are added in a 50.0 ml volumetric flask. The solution is sonicated in a sonicator for 5-10 minutes. The solution is heated in a water bath for 15-20 minutes at 60-70° C. The solution is cooled in room temperature for 5-10 minutes. The solution is transferred to a 25.0 ml volumetric flask. The total volume of 25.0 ml is made up with distilled water. The solution is filtered, and the analysis is proceeded.

Sample Solution Preparation: 500.0 mg of an herbal composition and 25.0 ml of water are added in a 50.0 ml volumetric flask. The solution is sonicated in a sonicator for 5-10 minutes. The solution is heated in a water bath for 15-20 minutes at 60-70° C. The solution is cooled in room temperature for 5-10 minutes. The solution is transferred to a 25.0 ml volumetric flask. The total volume of 25.0 ml is made up with distilled water. The solution is filtered, and the analysis is proceeded.

1.0 ml of standard and sample solutions are separately pipetted out in a 50.0 ml volumetric flask. 0.8 ml of salicylic acid-sulphuric acid reagent is added and mixed well. After 20 minutes, 19.0 ml of 2 N sodium hydroxide solution are added to raise the pH above 12. The solution is mixed well and cooled in room temperature. The absorbances of standard and sample solutions are measured in a UV spectrometer at 410.0 nm.

The analysis of turnitrates in *Brassica rapa* extract by UV spectrophotometer is described in more detail below.

Analysis of Turnitrates in *Brassica rapa* Extract by UV Spectrophotometer

Reagents Required:

Salicylic
acid
Sodium
hydroxide
Distilled
water
Concentrated Sulphuric acid

Salicylic Acid—Sulphuric Acid Reagent:

Dissolve 5 g of salicylic acid in 100 mL of Concentrated Sulphuric acid in a 200 ml beaker. Mix slowly, transfer to a brown bottle with lid. The salicylic acid-Sulphuric acid reagent should be made fresh every week and stored in a brown bottle.

2 N Sodium Hydroxide [NaOH]:

Weigh accurately about 40 g of Sodium hydroxide pellets in a 500 ml beaker. Add 100 ml of distilled water and sonicate the solution in a sonicator for 5-10 minutes. Transfer the solution to a 500 ml volumetric flask and make up the volume to 500 ml with distilled water.

Standard Solution Preparation: Weigh accurately about 200 mg *Brassica rapa* extract working standard (Prepared using botanically authenticated *Brassica rapa* roots), calibrate, and extract in 25 ml of water in a 50 ml volumetric flask. Sonicate the solution in a sonicator for 5-10 minutes and Heat the solution on water bath for 15-20 min at 60° C.-70° C. Cool the solution in room temperature for 5-10 minutes and make up the volume to 25 ml with water in a 25 ml standard flask. Filter and proceed with the analysis.

Sample Solution Preparation: Weigh accurately about 200 mg of a typical batch of *Brassica rapa* extract and extract in 25 ml of water in a 50 ml volumetric flask. Sonicate the solution in a sonicator for 5-10 minutes and Heat the solution on water bath for 15-20 min at 60° C.-70° C.

Cool the solution in room temperature for 5-10 minutes and make up the volume to 25 ml with water in a 25 ml standard flask. Filter and proceed with the analysis.

Pipette out 1 ml of standard and sample solutions separately in a 50 ml volumetric flask. Add 0.8 ml of Salicylic acid-Sulphuric acid reagent and mix well. After 20 minutes, add 19 ml of 2 N Sodium hydroxide solution to raise the pH above 12. Mix well and cool the solution at room temperature. Measure the absorbance of standard and sample solutions in UV spectrometer at 410 nm.

Blank Solution Preparation:

Pipette out 1 ml of water in a 50 ml volumetric flask and add 0.8 ml of concentrated sulphuric acid and 19 ml of 2 N Sodium hydroxide solution. Mix well and cool the solution at room temperature. Measure the absorbance of blank solution in UV spectrometer at 410 nm.

Protocol:

| Parameter | Volume of the solution (ml) | Volume of Salicylic acid - Sulphuric acid Solution (ml) | Volume of 2N Sodium hydroxide solution (ml) | Volume of Sulphuric acid solution (ml) |
|---|---|---|---|---|
| Standard solution | 1 ml | 0.8 ml | 19 ml | — |
| Sample solution | 1 ml | 0.8 ml | 19 ml | — |
| Blank solution | 1 ml [Water] | — | 19 ml | 0.8 ml |

Measure the absorbance of blank, standard and sample solutions in UV spectrometer at 410 nm and calculate the content of Turnitrates using the formula.

Calculation of Assay of Turnitrates:

$$\frac{\textit{Std}\text{ weight}}{\text{Sample weight}} \times \frac{\text{Sample Absorbance}}{\text{Standard Absorbance}} \times \%\text{ of Standard assay} = \%\text{ of }\textit{Turnitrates}\text{ in Sample}$$

Analysis of Bitters in *Momordica charantia* Extract by Gravimetry Method

Weigh accurately about 2.0 g of the sample and extract in about 50.0 ml of 100% methanol by refluxing it for 30 minutes in a water bath at 60° C.-70° C. Repeat this two more times and combine all the three extracts. Evaporate the extract to 50.0 ml on a water bath and transfer it to separating funnel, add 30.0 ml of water to the solution. Wash the aqueous alcoholic extract with two 25.0 ml portions of benzene in a separating flask and separate the layers and discard the benzene layer. Extract the aqueous alcoholic layer with 25.0 ml of ethyl acetate (4 times) in a separating flask. Combine the ethyl acetate layers in a tarred beaker, evaporate and dry the residue to constant weight at 90° C. in an oven.

Calculation:

$$\text{Percentage of Bitters content} = \frac{\text{Weight of the residue }[gm] \times 100 \times 100}{\text{Sample Weight }[gm] \times [100 - \text{Loss on Drying}]}$$

Analysis of Saponins in *Asparagus racemosus* Extract by Gravimetry Method

Weigh accurately about 3.0 gm of extract and transfer it to a 100 ml round bottom flask, fitted with reflux condenser. Charge 50 ml of 90% Methanol and reflux for 30 minutes. Cool, decant the clear extract and preserve. Repeat the extraction process twice using 30 ml of 90% Methanol each time.

Combine all the extracts, filter if necessary and concentrate the combined methanol up to about 5 ml, in a water bath. Precipitate this concentrated extract drop wise in 25 ml of acetone with continuous mixing.

This precipitate settles nicely and hence no need to filter. Decant the acetone solution carefully ensuring no precipitate is lost in acetone. Do not take out the precipitate from the beaker.

Discard the acetone solution. Dry the beaker along with the precipitate to constant weight in a hot air oven at 105° C.-110° C. Record the weight of the residue.

Saponins =

$$\frac{(\text{Weight of residue [g]})\times 100\times 100}{(\text{Sample weight [g]})\times(100-\text{loss on drying})} = \text{Saponins in sample}$$

Analysis of Tannins in *Phyllanthus niruri* Extract by Titration Method

Sample Preparation:

Weigh accurately about 0.1 g of extract and dissolve it in 50 ml of distilled water in a 250 ml volumetric flask. Mix well and sonicate the solution in a sonicator for 5-10 minutes in room temperature. Transfer the solution to a 1000 ml conical flask and add 750 ml of distilled water to the solution. Shake well and add 25 ml of Indigo carmine solution. Again, shake well and titrate the solution against 0.1 N Potassium permanganate solution ($KMnO_4$) slowly till a golden colour end point is attained.

Label the Titer value as A.

Carry out a blank titration by repeating the above with the same quantities of water and Indigo carmine solution in the same manner but omitting the sample.

Label the Titer value as B.

The difference between the two-titer values represents the indigo carmine solution required to neutralize the tannins.

Each ml of 0.1 N Potassium permanganate (KMnO4) is equivalent to 0.004157 gm of tannins.

Indigo Carmine Reagent Preparation:

Weigh accurately about 0.6 g of Indigo carmine and dissolve it in 20 ml of concentrated sulphuric acid in a 100 ml volumetric flask. Transfer the solution to a 500 ml measuring cylinder which should contain around 100 ml of water and make up the volume to 400 ml using distilled water.

Calculation:

Calculate the percentage of Tannins (W/W) as:

$$\frac{(A-B)\times 0.004157\times 100\times N}{\text{Wt of the Sample}\times 0.1}$$

A=Volume of 0.1 N Potassium permanganate consumed in titration for sample solution. B=Volume of 0.1 N Potassium permanganate consumed in titration for blank solution. N=Normality of potassium Permanganate (N/10) (0.1) W=weight of the sample taken in gm.

In some embodiments, an herbal composition is enriched in turnitrates. For example, the herbal composition may comprise no less than 0.1%, no less than 0.2%, no less than 0.3%, no less than 0.4%, no less than 0.5%, no less than 0.6%, no less than 0.7%, no less than 0.8%, no less than 0.9%, or no less than 1.0% of turnitrates in the composition. In some embodiments, an herbal composition comprises no less than 0.21%, no less than 0.22%, no less than 0.23%, no less than 0.24%, no less than 0.25%, no less than 0.26%, no less than 0.27%, no less than 0.28%, or no less than 0.29% of turnitrates in the composition, by weight relative to the total weight of the composition. In one embodiment, the herbal composition comprises no less than 0.25% of turnitrates in the composition.

In some embodiments, an herbal composition comprises from about 0.1% to about 3.0% of turnitrates, by weight relative to the total weight of the herbal composition. For example, an herbal composition may comprise from about 0.1% to about 2.0%, from about 0.1% to about 1.0%, from about 0.1% to about 0.5%, or from about 0.2% to about 0.4% of turnitrates, by weight relative to the total weight of the herbal composition.

In some embodiments, an herbal composition comprises from about 5% to about 30% of the *Brassica rapa* (turnip) extract, such as from about 5% to about 20%, from about 5% to about 15%, from about 10% to about 15%, from about 8% to about 13%, from about 9% to about 11%, from about 18% to about 22%, or from about 19% to about 21% of the *Brassica rapa* (turnip) extract, by weight relative to the total weight of the herbal composition.

In some embodiments of the present disclosure, an herbal composition comprises a *Momordica charantia* extract. In some embodiments, the *Momordica charantia* extract is an extract of *Momordica charantia* aerial parts. In some embodiments, the *Momordica charantia* aerial parts may be *Momordica charantia* fruits. In one embodiment, the *Momordica charantia* extract is an extract of *Momordica charantia* fruits.

In some embodiments, the *Momordica charantia* is dried and powdered before extraction. In some embodiments, the *Momordica charantia* is extracted with an extraction solvent chosen from water, alcohol, and combinations thereof. In some embodiments, the extraction solvent is water. In some embodiments, the extraction solvent is an alcohol, such as methanol, ethanol, propanol (such as isopropanol), butanol, or mixtures thereof. In some embodiments, the water is acidified with at least one acid. In some embodiments, the extraction solvent is an aqueous alcohol solution, such as aqueous ethanol, for example, 40%, 50%, 60%, 70%, or 80% ethanol in water (v/v). In some embodiments, the aqueous alcohol is acidified with at least one acid. In some embodiments, the weight ratio of *Momordica charantia* to extraction solvent is about 1:3. In some embodiments, the *Momordica charantia* is extracted at an elevated temperature, such as, for example, from about 75° C. to about 85° C. The *Momordica charantia* may be extracted more than once, such as three times, and the extracts may be combined and distilled. The distilled *Momordica charantia* extracts may be dried and further powdered to a fine mesh size. The powdered *Momordica charantia* extracts may be heat sterilized and sieved.

In some embodiments, the *Momordica charantia* extract comprises bitters. In some cases, the amount of bitters in *Momordica charantia* extract can be calculated by using a gravimetric method.

The amount of bitters can be calculated as follows:

$$\frac{\text{Weight of the residue [g]} \times 100 \times 100}{\text{Sample weight [g]} \times [100 - \text{Loss on Drying}]} = \text{\% of Bitters in Sample}$$

An exemplary gravimetric test may be conducted as below.

2.0 g of the *Momordica charantia* extract is placed in a round bottom flask, fitted with a reflux condenser. 50.0 ml of 100% methanol is charged and refluxed for 30 minutes in a water bath at 60-70° C. This extraction process is repeated twice. All three extracts are combined. The combined extract is evaporated and transferred to a separating funnel. 30.0 ml of water are added. The solution is washed with two 25.0 ml portions of benzene in a separating flask. The benzene layer is discarded. The aqueous alcoholic layer is extracted with 25.0 ml of ethyl acetate (four times) in a separating flask. The ethyl acetate layers are combined in a tarred beaker and evaporated. The residue is dried at 90° C. in an oven.

In some embodiments, an herbal composition is enriched in bitters. For example, the herbal composition may comprise no less than 0.5%, no less than 0.6%, no less than 0.7%, no less than 0.8%, no less than 0.9%, no less than 1.0%, no less than 1.1%, no less than 1.2%, no less than 1.3%, no less than 1.4%, no less than 1.5%, no less than 1.6%, no less than 1.7%, no less than 1.8%, no less than 1.9%, no less than 2.0%, no less than 2.1%, no less than 2.2%, no less than 2.3%, no less than 2.4%, or no less than 2.5% of bitters in the composition, by weight relative to the total weight of the composition. In one embodiment, the herbal composition comprises no less than 2% of bitters in the composition.

In some embodiments, an herbal composition comprises from about 1.0% to about 5.0% of bitters, by weight relative to the total weight of the herbal composition. For example, an herbal composition may comprise from about 1.0% to about 5.0%, from about 1.0% to about 4.0%, from about 1.0% to about 3.0%, or from about 2.0% to about 3.0% of bitters, by weight relative to the total weight of the herbal composition.

In some embodiments, an herbal composition comprises from about 5% to about 50% of a *Momordica charantia* extract, such as from about 10% to about 40%, from about 15% to about 40%, from about 20% to about 40%, from about 25% to about 35%, from about 28% to about 32%, from about 29% to about 31%, or from about 29.5% to about 30.5% of the *Momordica charantia* extract, by weight relative to the total weight of the herbal composition.

In some embodiments of the present disclosure, an herbal composition comprises a *Phyllanthus niruri* extract. In some embodiments, the *Phyllanthus niruri* extract is an extract of *Phyllanthus niruri* aerial parts.

In some embodiments, *Phyllanthus niruri* is dried and powdered before extraction. In some embodiments, the *Phyllanthus niruri* is extracted with an extraction solvent chosen from water, alcohol, and combinations thereof. In some embodiments, the extraction solvent is water. In some embodiments, the water is acidified with at least one acid. In some embodiments, the extraction solvent is an alcohol, such as methanol, ethanol, propanol (such as isopropanol), butanol, or mixtures thereof. In some embodiments, the extraction solvent is an aqueous alcohol solution, such as aqueous ethanol, for example, 40%, 50%, 60%, 70%, or 80% ethanol in water (v/v). In some embodiments, the aqueous alcohol is acidified with at least one acid. In some embodiments, the weight ratio of *Phyllanthus niruri* to extraction solvent is about 1:3. In some embodiments, the *Phyllanthus niruri* is extracted at an elevated temperature, such as, for example, from about 75° C. to about 85° C. The *Phyllanthus niruri* may be extracted more than once, such as three times, and the extracts may be combined and distilled. The distilled *Phyllanthus niruri* extracts may be dried and further powdered to a fine mesh size. The powdered *Phyllanthus niruri* extracts may be heat sterilized and sieved.

In some embodiments, the *Phyllanthus niruri* extract comprises tannins. The amount of tannins (W/W) in the composition may be determined by titration method. The amount of tannins (W/W) is:

$$\frac{(A - B) \times 0.004157 \times 100 \times N}{\text{Sample weight [g]} \times 0.1} = \text{\% of Tannins in Sample}$$

In the above equation, A is volume of 0.1 N potassium permanganate consumed in titration for sample solution. B is volume of 0.1 N potassium permanganate consumed in titration for blank solution. N is normality of potassium permanganate (N/10) (0.1). W is weight of the sample taken in g.

An exemplary titration may be conducted as follows:

Sample Preparation:

0.1 g of an extract is dissolved in 50.0 ml of distilled water in a 250.0 ml volumetric flask. The solution is mixed well and sonicated in a sonicator for 5-10 minutes in room temperature. The solution is transferred to a 1000.0 ml conical flask. 750.0 ml of distilled water are added to the solution. The solution is shaken well.

Weigh accurately about 0.6 g of Indigo carmine and dissolve it in 20 ml of concentrated sulphuric acid in 100 ml volumetric flask. Transfer the solution to a 500 ml measuring cylinder which should contain around 100 ml of water and make up the volume to 400 ml using distilled water.

25.0 ml of indigo carmine solution are added, and again, the solution is shaken well. The solution is titrated against 0.1 N potassium permanganate solution ($KMnO_4$) slowly until a golden color end point is attained. The titer value is labeled as A.

A blank titration is carried out by repeating the above with the same quantities of water and indigo carmine solution in the same manner but omitting the sample. The titer value is labeled as B.

The difference between the two titer values represents the indigo carmine solution required to neutralize the tannins. Each ml of 0.1 N potassium permanganate ($KMnO_4$) is equivalent to 0.004157 g of tannins.

In some embodiments, an herbal composition comprises enriched amounts of tannins. For example, the herbal composition may comprise no less than 0.5%, no less than 0.6%, no less than 0.7%, no less than 0.8%, no less than 0.9%, no less than 1.0%, no less than 1.1%, no less than 1.2%, no less than 1.3%, no less than 1.4%, no less than 1.5%, no less than 1.6%, no less than 1.7%, no less than 1.8%, no less than 1.9%, no less than 2.0%, no less than 2.1%, no less than 2.2%, no less than 2.3%, no less than 2.4%, or no less than 2.5% of tannins in the composition, by weight relative to the total weight of the composition. In one embodiment, the herbal composition comprises no less than 2.25% of tannins in the composition.

In some embodiments, an herbal composition comprises from about 1.0% to about 5.0% of tannins, by weight relative to the total weight of the herbal composition. For example, an herbal composition may comprise from about 1.0% to about 5.0%, from about 1.0% to about 4.0%, from about 2.0% to about 4.0%, or from about 2.0% to about 3.0% of tannins, by weight relative to the total weight of the herbal composition.

In some embodiments, an herbal composition comprises from about 5% to about 50% of a *Phyllanthus niruri* extract, such as from about 5% to about 30%, from about 35% to about 45%, from about 25% to about 30%, from about 10% to about 20%, from about 10% to about 15%, from about 15% to about 20%, from about 12% to about 18%, from about 13% to about 17%, from about 14% to about 16%, or from about 14.5% to about 15.5% of the *Phyllanthus niruri* extract, by weight relative to the total weight of the herbal composition.

In some embodiments of the present disclosure, the herbal composition comprises an *Asparagus racemosus* extract. In some embodiments, the *Asparagus racemosus* extract is an extract of *Asparagus racemosus* roots.

In some embodiments, *Asparagus racemosus* is dried and powdered before extraction. In some embodiments, the *Asparagus racemosus* is extracted with an extraction solvent chosen from water, alcohol, and combinations thereof. In some embodiments, the extraction solvent is water. In some embodiments, the extraction solvent is an alcohol, such as methanol, ethanol, propanol (such as isopropanol), butanol, or mixtures thereof. In some embodiments, the extraction solvent is an aqueous alcohol solution, such as aqueous ethanol, for example, 40%, 50%, 60%, 70%, or 80% ethanol in water (v/v). In some embodiments, the weight ratio of *Asparagus racemosus* to extraction solvent is about 1:3. In some embodiments, the *Asparagus racemosus* is extracted at an elevated temperature, such as, for example, from about 75° C. to about 85° C. *Asparagus racemosus* may be extracted more than once, such as three times, and the extracts may be combined and distilled. The distilled *Asparagus racemosus* extracts may be dried and further powdered to a fine mesh size. The powdered *Asparagus racemosus* extracts may be heat sterilized and sieved.

In some embodiments, the *Asparagus racemosus* extract comprises saponins. In some cases, the amount of saponins in *Asparagus racemosus* extract can be calculated by using a gravimetric method.

The amount of saponins can be calculated as follows:

$$\frac{\text{Weight of the residue [g]} \times 100 \times 100}{\text{Sample weight [g]} \times [100 - \text{Loss on Drying}]} = \text{\% of Saponins in Sample}$$

An exemplary gravimetric test may be conducted as follows.

3.0 g of an *Asparagus racemosus* extract is placed in a round bottom flask fitted with a reflux condenser. 50.0 ml of 90% methanol is charged and refluxed for 30 minutes. The solution is cooled. The clear extract is decanted and preserved. This extraction process is repeated twice. All three extracts are combined. The combined extract is filtered if necessary and concentrated in a water bath. The concentrated extract is precipitated dropwise in 25.0 ml acetone with continuous mixing. The acetone solution is decanted carefully to ensure no precipitate is lost in acetone. The beaker is dried along with the precipitate to a constant weight in a hot air oven at 105-110° C. The weight of the residue is recorded.

In some embodiments, an herbal composition is enriched in saponins. For example, the herbal composition may comprise no less than 0.5%, no less than 0.6%, no less than 0.7%, no less than 0.8%, no less than 0.9%, no less than 1.0%, no less than 1.1%, no less than 1.2%, no less than 1.3%, no less than 1.4%, no less than 1.5%, no less than 1.6%, no less than 1.7%, no less than 1.8%, no less than 1.9%, no less than 2.0%, no less than 2.1%, no less than 2.2%, no less than 2.3%, no less than 2.4%, no less than 2.5%, no less than 2.6%, no less than 2.7%, no less than 2.8%, no less than 2.9%, no less than 3.0%, no less than 3.1%, no less than 3.2%, no less than 3.3%, no less than 3.4%, no less than 3.5%, no less than 3.6%, no less than 3.7%, no less than 3.8%, no less than 3.9%, or no less than 4.0% of saponins in the composition, by weight relative to the total weight of the composition. In one embodiment, the herbal composition comprises no less than 3.75% of saponins in the composition.

In some embodiments, an herbal composition comprises from about 1.0% to about 5.0% of saponins, by weight relative to the total weight of the herbal composition. For example, an herbal composition may comprise from about 2.0% to about 5.0%, from about 3.0% to about 5.0%, from about 3.0% to about 4.0%, or from about 3.5% to about 5.0% of saponins, by weight relative to the total weight of the herbal composition.

In some embodiments, an herbal composition comprises from about 5% to about 50% of the *Asparagus racemosus* extract, such as from about 5% to about 30%, from about 35% to about 45%, from about 25% to about 30%, from about 10% to about 20%, from about 10% to about 15%, from about 15% to about 20%, from about 12% to about 18%, from about 13% to about 17%, from about 14% to about 16%, or from about 14.5% to about 15.5% of the *Asparagus racemosus* extract, by weight relative to the total weight of the herbal composition.

In an aspect of the present disclosure, an herbal composition comprises an *Andrographis paniculata* extract, a *Zingiber officinale* (ginger) extract, a *Brassica rapa* (turnip) extract, a *Momordica charantia* extract, an *Asparagus racemosus* extract, and a *Phyllanthus niruri* extract.

In another aspect of the present disclosure, the herbal composition further comprises at least one pharmaceutically acceptable excipient. In some embodiments, the herbal composition consists essentially of the *Andrographis paniculata* extract, the *Zingiber officinale* (ginger) extract, the *Brassica rapa* (turnip) extract, the *Momordica charantia* extract, the *Asparagus racemosus* extract, and the *Phyllanthus niruri* extract and, optionally, at least one pharmaceutically acceptable excipient. In some embodiments, the herbal composition consists of the *Andrographis paniculata* extract, the *Zingiber officinale* (ginger) extract, the *Brassica rapa* (turnip) extract, the *Momordica charantia* extract, the *Asparagus racemosus* extract, and the *Phyllanthus niruri* extract.

In some embodiments, the composition further comprises a turmeric extract, a garlic extract, a green tea extract, a milk thistle extract, a *Terminalia arjuna* extract, a kutki extract, a *ginseng* extract, or any combination thereof. In some embodiments, the composition further comprises at least one pharmaceutically acceptable excipient or antioxidant. In some embodiments, the composition is a dietary supplement.

In some embodiments, an herbal composition comprises an *Andrographis paniculata* extract, a *Zingiber officinale* (ginger) extract, and a *Brassica rapa* (turnip) extract.

In some embodiments, the weight ratio of the *Andrographis paniculata* extract to the *Zingiber officinale* (ginger) extract ranges from about 1.5:1 to about 2.5:1, such as from about 1.6:1 to about 2.4:1, from about 1.7:1 to about 2.3:1, from about 1.8:1 to about 2.2:1, or from about 1.9:1 to about 2.1:1. In some embodiments, the weight ratio of the *Andrographis paniculata* extract to the *Zingiber officinale* (ginger) extract is about 2:1.

In some embodiments, the weight ratio of the *Andrographis paniculata* extract to the *Brassica rapa* (turnip) extract ranges from about 1.5:1 to about 2.5:1, such as from about 1.6:1 to about 2.4:1, from about 1.7:1 to about 2.3:1, from about 1.8:1 to about 2.2:1, or from about 1.9:1 to about 2.1:1. In some embodiments, the weight ratio of the *Andrographis paniculata* extract to the *Brassica rapa* (turnip) extract is about 2:1.

In some embodiments, the weight ratio of the *Zingiber officinale* (ginger) extract to the *Brassica rapa* (turnip) extract ranges from about 0.5:1 to about 1.5:1, such as from about 0.6:1 to about 1.4:1, from about 0.7:1 to about 1.3:1, from about 0.8:1 to about 1.2:1, or from about 0.9:1 to about 1.1:1. In some embodiments, the weight ratio of the *Zingiber officinale* (ginger) extract to the *Brassica rapa* (turnip) extract is about 1:1.

In some embodiments, the herbal composition further comprises a *Momordica charantia* extract, an *Asparagus racemosus* extract, and/or a *Phyllanthus niruri* extract. In some embodiments, an herbal composition comprises an *Andrographis paniculata* extract, a *Zingiber officinale* (ginger) extract, a *Brassica rapa* (turnip) extract, a *Momordica charantia* extract, an *Asparagus racemosus* extract, and a *Phyllanthus niruri* extract, and, optionally, at least one pharmaceutically acceptable excipient.

In some embodiments, an herbal composition comprises from about 15% to about 25% of the *Andrographis paniculata* extract, from about 5% to about 15% of the *Zingiber officinale* (ginger) extract, from about 5% to about 15% of the *Brassica rapa* (turnip) extract, from about 25% to about 35% of the *Momordica charantia* extract, from about 10% to about 20% of the *Asparagus racemosus* extract, and from about 10% to about 20% of the *Phyllanthus niruri* extract, by weight relative to the total weight of the composition.

In some embodiments, an herbal composition comprises from about 18% to about 22% of the *Andrographis paniculata* extract, from about 8% to about 12% of the *Zingiber officinale* (ginger) extract, from about 8% to about 12% of the *Brassica rapa* (turnip) extract, from about 28% to about 32% of the *Momordica charantia* extract, from about 13% to about 18% of the *Asparagus racemosus* extract, and from about 13% to about 18% of the *Phyllanthus niruri* extract, by weight relative to the total weight of the composition.

In some embodiments, an herbal composition comprises from about 19% to about 21% of the *Andrographis paniculata* extract, from about 9% to about 11% of the *Zingiber officinale* (ginger) extract, from about 9% to about 11% of the *Brassica rapa* (turnip) extract, from about 29% to about 31% of the *Momordica charantia* extract, from about 14% to about 16% of the *Asparagus racemosus* extract, and from about 14% to about 16% of the *Phyllanthus niruri* extract, by weight relative to the total weight of the composition.

In some embodiments, an herbal composition comprises about 20% of the *Andrographis paniculata* extract, about 10% of the *Zingiber officinale* (ginger) extract, about 10% of the *Brassica rapa* (turnip) extract, about 30% of the *Momordica charantia* extract, about 15% of the *Asparagus racemosus* extract, and about 15% of the *Phyllanthus niruri* extract, by weight relative to the total weight of the composition.

In some embodiments, the herbal composition comprises from about 10% to about 50% of the *Andrographis paniculata* extract, by weight relative to the total weight of the herbal composition, such as from about 10% to about 40%, from about 20% to about 40%, from about 15% to about 30%, from about 15% to about 25%, from about 18% to about 22%, or from about 19% to about 21% of the *Andrographis paniculata* extract, by weight relative to the total weight of the herbal composition.

In some embodiments, the herbal composition comprises from about 5% to about 30% of the *Zingiber officinale* (ginger) extract, such as from about 5% to about 20%, from about 5% to about 15%, from about 10% to about 15%, from about 8% to about 13%, from about 9% to about 11%, from about 18% to about 22%, or from about 19% to about 21% of the *Zingiber officinale* (ginger) extract, by weight relative to the total weight of the herbal composition.

In some embodiments, the herbal composition comprises from about 5% to about 30% of the *Brassica rapa* (turnip) extract, such as from about 5% to about 20%, from about 5% to about 15%, from about 10% to about 15%, from about 8% to about 13%, from about 9% to about 11%, from about 18% to about 22%, or from about 19% to about 21% of the *Brassica rapa* (turnip) extract, by weight relative to the total weight of the herbal composition.

In some embodiments, the herbal composition comprises from about 5% to about 50% of the *Momordica charantia* extract, such as from about 10% to about 40%, from about 15% to about 40%, from about 20% to about 40%, from about 25% to about 35%, from about 28% to about 32%, from about 29% to about 31%, or from about 29.5% to about 30.5% of the *Momordica charantia* extract, by weight relative to the total weight of the herbal composition.

In some embodiments, the herbal composition comprises from about 5% to about 50% of the *Asparagus racemosus* extract, such as from about 5% to about 30%, from about 35% to about 45%, from about 25% to about 30%, from about 10% to about 20%, from about 10% to about 15%, from about 15% to about 20%, from about 12% to about 18%, from about 13% to about 17%, from about 14% to about 16%, or from about 14.5% to about 15.5% of the *Asparagus racemosus* extract, by weight relative to the total weight of the herbal composition.

In some embodiments, the herbal composition comprises from about 5% to about 50% of the *Phyllanthus niruri* extract, such as from about 5% to about 30%, from about 35% to about 45%, from about 25% to about 30%, from about 10% to about 20%, from about 10% to about 15%, from about 15% to about 20%, from about 12% to about 18%, from about 13% to about 17%, from about 14% to about 16%, or from about 14.5% to about 15.5% of the *Phyllanthus niruri* extract, by weight relative to the total weight of the herbal composition.

In some embodiments, the herbal composition does not comprise a natural oil, such as flax seed oil, sesame seed oil, castor oil, sunflower oil, soybean oil, safflower oil, corn oil, hemp oil, palm oil, or peanut oil.

In some embodiments, the herbal compositions of the present disclosure may comprise at least one pharmaceutically acceptable excipient, for example, to thicken, dilute, emulsify, stabilize, preserve, protect, color, flavor, and/or fashion the herbal extracts into an applicable and efficacious preparation, such that it may be safe, convenient, and/or otherwise acceptable for use. In some embodiments, the herbal composition may comprise from about 0% to about 10% of at least one pharmaceutically acceptable excipient, such as from about 0.5% to about 5% of at least one pharmaceutically acceptable excipient, by weight relative to the total weight of the herbal composition.

In some embodiments, the herbal composition comprises less than 5%, such as less than 4%, less than 3%, less than 2%, or less than 1% of pharmaceutically acceptable excipients and/or residual extraction solvent, by weight relative to the total weight of the herbal composition.

In some embodiments, the herbal compositions of the present disclosure may further comprise at least one antioxidant. Examples of antioxidants suitable for the present disclosure include, but are not limited to, alpha-tocopherol (vitamin E), calcium disodium EDTA, alpha tocoferylacetates, butylhydroxytoluenes (BHTs), butylhydroxyanisoles (BHAs), green tea extract, grape seed extract, *Ginkgo biloba* extract, blueberry extract, rosemary extract, and any combinations thereof.

The herbal compositions of the present disclosure may be administered to a subject via an oral route. Thus, in one aspect, the present disclosure is directed to a dosage form for oral administration comprising an herbal composition according to the present disclosure. In some embodiments, the herbal compositions of the present disclosure may be provided in any form suitable for oral administration, such as, for example, in the form of a pill, capsule, tablet, sachet, oral solution, or oral suspension. The dosage forms can be prepared according to processes known in the art and may include one or more pharmaceutically acceptable excipients, as discussed above.

In some embodiments, the dosage form is a dosage form for oral administration comprising an herbal composition of the present disclosure. The herbal composition may be any herbal composition of the present disclosure, such as, for example, any of the herbal compositions discussed above. In some embodiments, the dosage form may be a pill, a tablet, a capsule, an oral solution, an oral suspension, an oral spray, or any other dosage form suitable for oral administration. The dosage form may be solid or liquid. When solid, the dosage form may be of any size and shape suitable for oral administration. In some embodiments, the dosage form is a capsule. In some embodiments, the capsule is a gelatin capsule, a polysaccharide capsule, or a vegetarian capsule. The capsule may be a hard capsule or a soft capsule. In some embodiments, the dosage form for oral administration further comprises at least one pharmaceutically acceptable excipient, as discussed above.

The present disclosure further encompasses methods of supporting, maintaining, or improving liver health by administering an effective amount of an herbal composition of the present disclosure to a subject. Thus, in one aspect, the present disclosure is directed to a method of supporting, maintaining, or improving liver health in a subject, comprising administering to the subject an effective amount of an herbal composition of the present disclosure. Another embodiment of the present disclosure encompasses methods of supporting, maintaining, or improving liver health by administering an effective amount of an herbal composition of the present disclosure to a subject in need thereof. For example, an effective amount may be an amount that supports, maintains, or improves liver function, resulting in a reduction of at least one liver enzyme level chosen from alanine aminotransferase (formerly called serum glutamic pyruvic transaminase (ALT/SGPT)), aspartate aminotransferase, also known as serum glutamic oxaloacetic transaminase (AST/SGOT), bilirubin, and alkaline phosphatase (ALP) levels, as measured using the assay methods. The herbal composition may be any herbal composition of the present disclosure, such as, for example, any of the herbal compositions discussed above.

For example, in some embodiments, there is provided a method of supporting, maintaining, or improving liver health in a subject, comprising administering to the subject an herbal composition comprising an *Andrographis paniculata* extract, a *Zingiber officinale* (ginger) extract, a *Brassica rapa* (turnip) extract, a *Momordica charantia* extract, an *Asparagus racemosus* extract, and a *Phyllanthus niruri* extract. For example, in some embodiments, the method comprises administering to the subject about 1.0 g/day of an herbal composition comprising from about 15% to about 25% of the *Andrographis paniculata* extract, from about 5% to about 15% of the *Zingiber officinale* (ginger) extract, from about 5% to about 15% of the *Brassica rapa* (turnip) extract, from about 25% to about 35% of the *Momordica charantia* extract, from about 10% to about 20% of the *Asparagus racemosus* extract, and from about 10% to about 20% of the *Phyllanthus niruri* extract, by weight relative to the total weight of the composition.

In some embodiments, the herbal composition of the present disclosure is administered orally. In some embodiments, the oral daily dosage of the herbal composition ranges from about 0.1 g to about 4.0 g, such as from about 0.5 g to about 4.0 g, from about 0.5 g to about 3.0 g, from about 0.5 g to about 2.0 g, from about 0.5 g to about 1.5 g, from about 0.5 g to about 1.2 g, from about 0.8 g to about 4.0 g, from about 0.8 g to about 3.0 g, from about 0.8 g to about 2.0 g, from about 0.8 g to about 1.5 g, or from about 0.8 g to about 1.2 g per day. For example, in some embodiments, the daily dosage of the herbal composition is about 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, or 4.0 g per day orally. In some embodiments, the daily dosage is about 1.0 g per day orally.

In some embodiments of one aspect, the herbal composition is administered orally one, two, three, or more than three times per day. In some embodiments, the herbal composition is administered twice per day orally. For example, in some embodiments, about 0.5 g of the herbal composition is administered orally twice per day, for a total daily dosage of about 1.0 g per day. In other embodiments, about 1.0 g of the herbal composition is administered orally once per day, for a total daily dose of about 1.0 g per day. In some embodiments, the herbal composition is administered orally for at least 30 days, such as for at least 60 days, at least 90 days, at least 120 days, or longer.

As discussed above, the herbal compositions of the present disclosure may be administered orally in any form suitable for oral administration. For example, in some embodiments, the herbal composition may be administered to the subject in the form of a powder, a pill, a tablet, a capsule, an oral solution, an oral suspension, or in any other form suitable for oral administration. In some embodiments, the herbal composition is administered in capsule form. For example, in some embodiments, a capsule comprising about 0.5 g of the herbal composition may be administered twice per day to provide a total daily dosage of about 1.0 g of the herbal composition. In another embodiment, a capsule comprising about 1.0 g of the herbal composition may be administered once per day, for a total daily dosage of about 1.0 g of the herbal composition.

In some embodiments, the herbal compositions of the present disclosure support, maintain, or improve liver function, resulting in a reduction of at least one liver enzyme level chosen from alanine aminotransferase (formerly called serum glutamic pyruvic transaminase (ALT/SGPT)), aspartate aminotransferase, also known as serum glutamic oxaloacetic transaminase (AST/SGOT), bilirubin, and alkaline phosphatase (ALP) levels.

In some embodiments, the herbal compositions of the present disclosure, when administered for a certain period, reduce at least 20%, 25%, 30%, 35%, 40%, 45%, or 50% of ALT levels. In some of the embodiments, the herbal compositions of the present disclosure reduce at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50% of ALT levels.

In some embodiments, an herbal composition may reduce from about 10% to about 60% of ALT levels in a subject, when administered for a certain period. For example, an herbal composition may reduce from about 20% to about 60%, from about 30% to about 60%, from about 35% to about 50%, from about 35% to about 45%, from about 40% to about 50%, or from about 45% to about 55% of ALT levels in a subject.

In some embodiments, the herbal compositions of the present disclosure, when administered for a certain period, reduce at least 20%, at least 25%, at least 30%, at least 35%, at least 40%, at least 45%, at least 50%, at least 53%, at least 55%, at least 60%, at least 65%, or at least 70% of AST levels. In some of the embodiments, the herbal compositions reduce at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, or at least 60% of AST levels.

In some embodiments, an herbal composition may reduce from about 10% to about 70% of AST levels in a subject, when administered for a certain period. For example, an herbal composition may reduce from about 20% to about 70%, from about 30% to about 60%, from about 40% to about 60%, from about 50% to about 65%, or from about 53% to about 55% of AST levels in a subject.

In some embodiments, the herbal compositions of the present disclosure, when administered fora certain period, reduce at least 10%, at least 15%, at least 20%, at least 25%, at least 30%, at least 35%, or at least 40% of ALP levels. In some of the embodiments, the herbal compositions reduce at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% of ALP levels.

In some embodiments, an herbal composition may reduce from about 10% to about 50% of ALP levels in a subject, when administered for a certain period. For example, an herbal composition may reduce from about 10% to about 35%, from about 15% to about 30%, from about 20% to about 30%, from about 20% to about 25%, or from about 20% to about 22% of ALP levels in a subject.

In some embodiments, the herbal compositions of the present disclosure, when administered fora certain period, reduce at least 10%, at least 15%, at least 20%, at least 25%, at least 30%, at least 35%, or at least 40% of blood bilirubin levels. In some of the embodiments, the herbal compositions reduce at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% of blood bilirubin levels.

In some embodiments, an herbal composition may reduce from about 10% to about 50% of blood bilirubin levels in a subject, when administered for a certain period. For example, an herbal composition may reduce from about 10% to about 35%, from about 15% to about 30%, from about 15% to about 25%, from about 18% to about 23%, or from about 19% to about 21% of blood bilirubin levels in a subject.

In some embodiments, the herbal compositions of the present disclosure, when administered fora certain period, reduce at least 10%, at least 15%, at least 20%, at least 25%, at least 30%, at least 35%, or at least 40% of malondialdehyde (MDA) levels. In some of the embodiments, the herbal compositions reduce at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% of malondialdehyde (MDA) levels.

In some embodiments, an herbal composition may reduce from about 10% to about 50% of malondialdehyde (MDA) levels in a subject, when administered for a certain period. For example, an herbal composition may reduce from about 10% to about 35%, from about 15% to about 30%, from about 15% to about 25%, from about 18% to about 27%, or from about 25% to about 35% of malondialdehyde (MDA) levels in a subject.

In some embodiments, the herbal compositions of the present disclosure, when administered for a certain period, increase at least 10%, at least 15%, at least 20%, at least 25%, at least 30%, at least 35%, or at least 40% of superoxide dismutase (SOD) levels. In some of the embodiments, the herbal compositions increase at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% of superoxide dismutase (SOD) levels.

In some embodiments, an herbal composition may increase from about 10% to about 50% of superoxide dismutase (SOD) levels in a subject, when administered for a certain period. For example, an herbal composition may increase from about 10% to about 35%, from about 15% to about 30%, from about 15% to about 25%, from about 18% to about 23%, or from about 19% to about 21% of superoxide dismutase (SOD) levels in a subject.

In some embodiments, the herbal compositions of the present disclosure, when administered fora certain period, reduce at least 10%, at least 15%, at least 20%, at least 25%, at least 30%, at least 35%, or at least 40% of gamma-glutamyl transferase (GGT) levels. In some of the embodiments, the herbal compositions reduce at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% of gamma-glutamyl transferase (GGT) levels.

In some embodiments, an herbal composition may reduce from about 10% to about 50% of gamma-glutamyl transferase (GGT) levels in a subject, when administered for a certain period. For example, an herbal composition may reduce from about 10% to about 35%, from about 15% to about 30%, from about 15% to about 25%, from about 18% to about 23%, or from about 19% to about 21% of gamma-glutamyl transferase (GGT) levels in a subject.

In one aspect, the present disclosure is directed to a method of making an herbal composition comprising: extracting *Andrographis paniculata* aerial parts to form an *Andrographis paniculata* extract, extracting *Zingiber officinale* (ginger) rhizomes to form a *Zingiber officinale* (ginger) extract, extracting *Momordica charantia* fruits to form a

*Momordica charantia* extract, extracting *Brassica rapa* (turnip) to form a *Brassica rapa* (turnip) extract, extracting *Asparagus racemosus* roots to form an *Asparagus racemosus* extract, and extracting *Phyllanthus niruri* aerial parts to form a *Phyllanthus niruri* extract; combining the *Andrographis paniculata* extract, the *Zingiber officinale* (ginger) extract, the *Momordica charantia* extract, the *Brassica rapa* (turnip) extract, the *Asparagus racemosus* extract, and the *Phyllanthus niruri* extract; and blending the combined extracts.

In some embodiments, herbal parts are dried and powdered before extraction. In some embodiments, the herbal parts are extracted with an extraction solvent chosen from water, alcohol, and combinations thereof. In some embodiments, the extraction solvent is water. In some embodiments, the water is acidified with at least one acid. In some embodiments, the extraction solvent is an alcohol, such as methanol, ethanol, propanol (such as isopropanol), butanol, or mixtures thereof. In some embodiments, the extraction solvent comprises at least one aqueous alcohol, such as aqueous methanol, aqueous ethanol, or combinations thereof. In some embodiments, the aqueous alcohol is acidified with at least one acid. In some embodiments, the aqueous alcohol comprises at least about 1% alcohol by volume, such as at least about 5%, 10%, 15%, 20%, 30%, 40%, 50%, 60%, 70%, 80%, 90%, or at least about 95% alcohol by volume. In some embodiments, the aqueous alcohol comprises at least about 5% water by volume, such as at least about 10%, 15%, 20%, 30%, 40%, 50%, 60%, 70%, 80%, 90%, 95%, or at least about 99% water by volume. In some embodiments, the aqueous alcohol comprises from about 5% to about 99% water and from about 95% to about 1% alcohol by volume. In some embodiments, the aqueous alcohol comprises from about 50% to about 95% water and from about 50% to about 5% alcohol by volume, such as from about 50% to about 95% water and from about 50% to about 5% ethanol by volume. In some embodiments, the aqueous alcohol comprises about 95% water and about 5% ethanol, about 90% water and about 10% ethanol, about 85% water and about 15% ethanol, about 80% water and about 20% ethanol, about 75% water and about 25% ethanol, about 70% water and about 30% ethanol, about 65% water and about 35% ethanol, about 60% water and about 40% ethanol, about 55% water and about 45% ethanol, about 50% water and about 50% ethanol, about 40% water and about 60% ethanol, about 30% water and about 70% ethanol, or about 20% water and about 80% ethanol by volume. In one embodiment, the extraction solvent comprises about 60% water and about 40% ethanol by volume.

In some embodiments, the weight ratio of herbal parts to extraction solvent ranges from about 1:10 to about 1:2, such as from about 1:10 to about 1:3, from about 1:10 to about 1:5, from about 1:5 to about 1:2, from about 1:5 to about 1:3, or from about 1:3 to about 1:2. In some embodiments, the weight ratio of herbal parts to extraction solvent is about 1:10. In some embodiments, the weight ratio of herbal parts to extraction solvent is about 1:5. In some embodiments, the weight ratio of herbal parts to extraction solvent is about 1:3.

In some embodiments, the extraction may be carried out at ambient temperature. In some embodiments, the extraction may be carried out at a temperature within the range of from about 15° C. to about 35° C. In some embodiments, the extraction may be carried out at an elevated temperature, such as, for example, from about 35° C. to about 95° C., from about 65° C. to about 95° C., from about 70° C. to about 90° C., or from about 75° C. to about 85° C. In some embodiments, the herbal parts are extracted once. In some embodiments, the herbal parts are extracted multiple times, such as at least two times, at least three times, or more than three times. In some embodiments, aqueous ethanol or water is added to residue of the first extract for further extraction. In some embodiments, aqueous ethanol or water is added to residue of the second extract for further extraction. When the extraction is performed multiple times, each of the individual extracts may be combined, and the combined extracts may be concentrated to remove the extraction solvent.

The herbal extracts may be concentrated to remove extraction solvents before further drying. In some embodiments, the herbal extracts may be concentrated using distillation. The herbal extracts may be concentrated in a stainless-steel reactor with an agitator, a thin film evaporator, an agitated wiped film evaporator, a calandria distillation unit, a vacuum distillation assembly, or any distillation vessel with a vacuum facility. The concentrated extracts may be dried. For example, the concentrated extract may be dried in a tray drier at 90-100° C. or spray dried by maintaining an outlet temperature of 90-100° C. The herbal extracts may be further powdered in a multi-mill or pulverized to a fine mesh size. The powdered extracts may be sterilized. In some embodiments, heat sterilization may be used. In some embodiments, filtration, radiation, or light may be used. The extracts may be sieved before being packaged.

The herbal extracts of the present disclosure may comprise various active ingredients, such as livolides, bitters, saponins, tannins, turnitrates, and zinzirols. The various active ingredients of the herbal extracts may be enriched by selective extraction. In some embodiments, the active ingredients may be isolated and characterized by at least one method chosen from column chromatography, high pressure liquid chromatography (HPLC), thin layer chromatography (TLC), fractional separation, gradient precipitation, crystallization, washing, or derivatization.

In some embodiments, the active ingredients may be identified using high performance thin layer chromatography (HPTLC), high pressure liquid chromatography (HPLC), gas chromatography (GC), medium pressure liquid chromatography (MPLC), column chromatography, liquid chromatography with mass spectrometry (LCMS-MS), gas chromatography with mass spectrometry (LCMS-MS), a UV method, inductively coupled plasma mass spectrometry (ICP-MS), a gravimetric method, or a titration method.

In some embodiments, an herbal composition is comprised in a pharmaceutical kit. In one embodiment, kits comprising unit doses of at least one composition of the present disclosure, for example, in oral or injectable doses, are provided. Such kits may include a container comprising the unit dose, an informational package insert describing the use and attendant benefits of the therapeutic in treating the liver condition of interest, and/or optionally an appliance or device for delivery of the at least one herbal composition and/or pharmaceutical composition comprising the same.

Other than in the examples, or where otherwise indicated, all numbers expressing quantities of ingredients, reaction conditions, analytical measurements, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated, the numerical values set forth in the specific examples are reported as precisely as possible. Any numerical value, however, inherently contains certain errors necessarily resulting from the standard deviation found in their respective testing measurements.

The compositions and methods described herein will be further described by the following nonlimiting examples, which are intended to be purely exemplary. It is understood that the skilled artisan will envision additional embodiments consistent with the disclosure provided herein.

Example 1: Preparing Herbal Extracts

This example provides an exemplary protocol for preparing various herbal extracts described herein.

FIG. 1 illustrates an exemplary process to produce an *Andrographis paniculata* extract.

First, *Andrographis paniculata* aerial parts were dried and coarsely powdered. The dried and powdered *Andrographis paniculata* aerial parts were charged in a 5000-liter extractor along with 3000 liters of aqueous ethanol and heated for 4-5 hours at 75-85° C. The mixture was cooled to below 60° C. and filtered to recover a first extract.

Next, 3000 liters of aqueous ethanol (v/v) was added to the marc from the first extraction and heated for 4-5 hours at 75-85° C. The mixture was cooled to below 60° C. and filtered to recover a second extract.

Next, 3000 liters of water was added to the marc from the second extraction and heated for 4-5 hours at 85-95° C. The mixture was cooled to below 60° C. and filtered to recover a third extract.

All three extracts were concentrated in a stainless-steel reactor and combined. The combined, concentrated extract was dried in a tray drier at 90-100° C. or spray dried by maintaining an outlet temperature of 90-100° C. The dried extract was further powdered in a multi-mill or pulverized to a fine mesh size. It was sieved using a sifter to achieve a uniform particle size and blended in an octagonal blender to achieve uniformity. Finally, the product was heat sterilized and sieved again. It was packed in food grade, virgin, double polyethylene bags and placed in an export worthy drum.

A *Zingiber officinale* (ginger) extract was produced using the same process described above for the *Andrographis paniculata* extract, except that *Zingiber officinale* (ginger) rhizomes were used instead of *Andrographis paniculata* aerial parts.

A *Momordica charantia* extract was produced using the same process described above for the *Andrographis paniculata* extract, except that *Momordica charantia* fruits were used instead of *Andrographis paniculata* aerial parts.

A *Brassica rapa* (turnip) extract was produced using the same process described above for the *Andrographis paniculata* extract, except that turnip roots were used instead of *Andrographis paniculata* aerial parts.

A *Phyllanthus niruri* extract was produced using the same process described above for the *Andrographis paniculata* extract, except that *Phyllanthus niruri* aerial parts were used instead of *Andrographis paniculata* aerial parts.

An *Asparagus racemosus* extract was produced using a different extraction medium. As the first step, *Asparagus racemosus* roots were dried and powdered. This is treated with boiling water many times, purified, and dried. The rest of the steps are the same as the steps for producing an *Andrographis paniculata* extract, except that water is only used instead of aqueous ethanol.

Each extract is combined. The combined ingredients were sieved using a sifter to achieve a uniform particle size and blended to achieve a uniform mixture. Finally, the product was heat sterilized, sieved again, and packed.

Example 2: Preparing Composition A

Figure 2:
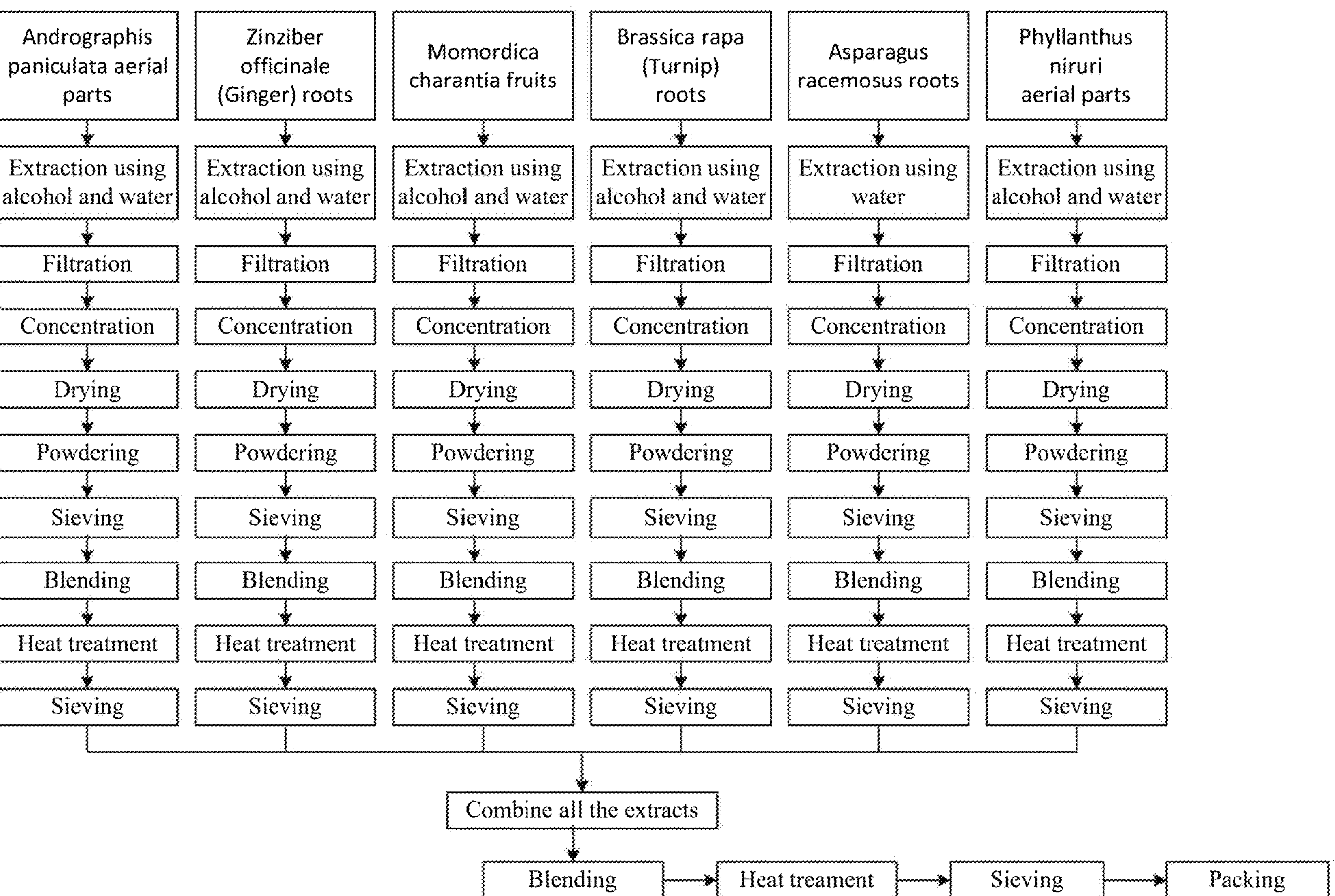
FIG. 2 illustrates an exemplary process for preparing an herbal composition according to the present disclosure.

FIG. 2 illustrates an exemplary process for preparing Composition A. Each extract prepared in Example 1 is combined. The combined ingredients were sieved using a sifter to achieve a uniform particle size and blended to achieve a uniform mixture. Finally, the product was heat sterilized, sieved again, and packed.

The ingredients and each of the amounts in Composition A are below.

| Composition A Ingredients | Amount |
|---|---|
| Andrographis paniculata extract | 20% |
| Zingiber officinale (ginger) extract | 10% |
| Momordica charantia extract | 30% |
| Brassica rapa (turnip) extract | 10% |
| Asparagus racemosus extract | 15% |
| Phyllanthus niruri extract | 15% |
| Total | 100% |

Example 3: Identification of Active Ingredients

Livolides

An *Andrographis paniculata* extract contains livolides. The presence of livolides in Composition A is confirmed by HPTLC. Details are given below.

Instrument: CAMAG High Performance Thin Layer Chromatography System (HPTLC) comprising: Applicator—Linomat 5, Digistore—2, Multiwavelength Scanner, Transparent Chromatographic Tank, and HPTLC pre-coated silica plate, Silica Gel 60 F254, 10.0×10.0 cm (Merck).

Working Standard Preparation A: 500.0 mg of Composition A working standard [KLF/WS/01] is dissolved in 30.0 ml 95% methanol for 30 minutes in a water bath at 70-80° C. Filter and concentrate to 5.0 ml. Proceed for spotting.

Working Standard Preparation B: 300.0 mg of *Andrographis paniculata* extract working standard [AND/WS/18] (prepared using botanically authenticated *Andrographis paniculata* aerial parts) is dissolved in 30.0 ml 95% methanol for 30 minutes in a water bath at 70-80° C. Filter and concentrate to 5.0 ml. Proceed for spotting.

Sample Preparation C: 500.0 mg of a typical batch of Composition A [KLF/20001] is dissolved in 30.0 ml 95% methanol for 30 minutes in a water bath at 70-80° C. Filter and concentrate to 5.0 ml. Proceed for spotting.

Mobile Phase:

Chloroform:acetone:toluene [2:2:1].

Chromatography:

1. Transfer 10.0 ml of a mixture of chloroform:acetone:toluene [2:2:1] to the chromatographic tank. Place a Whatman filter paper disc in the chromatographic tank and close with the lid (for faster saturation of the tank with the solvent system). Allow the tank to saturate for 30 minutes.

2. Apply 5.0 μl of sample(s) and 5.0 μl Standard (as 10.0 mm bands separated by a distance of 15.0 mm, at 10.0 mm from the base) on an HPTLC silica plate using a Linomat HPTLC applicator.

3. Leave the plate in a fume hood to allow the solvent to evaporate. Place the plate in the tank as near vertical as possible, ensuring that the line of application is well above the solvent level. Replace the lid tightly and allow the solvent to ascend to 1.5 cm below the top of the plate.

4. Remove the plate and let it air dry in the fume hood.

Detection: UV 366 nm, after spraying vanillin-sulphuric acid [white light].

Figure 3:
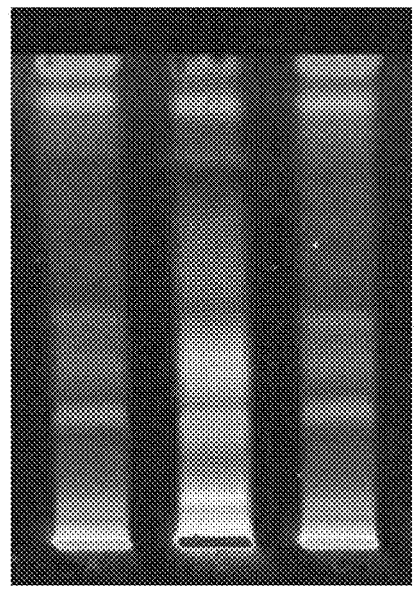
FIG. 3 illustrates an identification of livolides in an herbal composition by high performance thin layer chromatography (HPTLC) fingerprinting.
Figure 3:
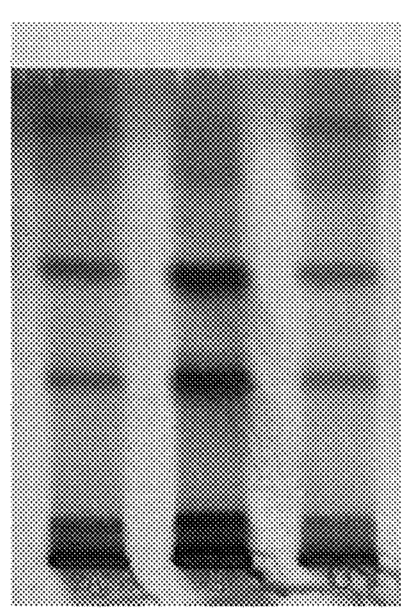

Conclusion: As illustrated in FIG. 3, HPTLC fingerprinting of a typical batch of Composition A [KLF/20001] matches with Composition A working standard [KLF/WS/01]. Bands observed in Composition A [KLF/20001] are present in *Andrographis paniculata* extract working standard containing livolides. These findings confirm that Composition A [KLF/20001] contains livolides.

Zinzirols

A *Zingiber officinale* (ginger) extract contains zinzirols. Presence of zinzirols in Composition A is confirmed by HPTLC. Details are given below.

Instrument: CAMAG High Performance Thin Layer Chromatography System (HPTLC) comprising: Applicator—Linomat 5, Digistore—2, Multiwavelength Scanner, Transparent Chromatographic Tank, and HPTLC pre-coated silica plate, Silica Gel 60 F254, 10.0×10.0 cm (Merck).

Working Standard Preparation A: 500.0 mg of Composition A working standard [KLF/WS/01] is dissolved in 30.0 ml 95% methanol for 30 minutes in a water bath at 70-80° C. Filter and concentrate to 5.0 ml. Proceed for spotting.

Working Standard Preparation B: 300.0 mg of *Zingiber officinale* (ginger) extract working standard [GDE/WS/17] [prepared by using *Zingiber officinale* (ginger) roots (rhizomes)] is dissolved in 30.0 ml 95% methanol for 30 minutes in a water bath at 70-80° C. Filter and concentrate to 5.0 ml. Proceed for spotting.

Sample Preparation C: 500.0 mg of Composition A [KLF/20001] is dissolved in 30.0 ml 95% methanol for 30 minutes in a water bath at 70-80° C. Filter and concentrate to 5.0 ml. Proceed for spotting.

Mobile Phase:

Benzene:ethyl acetate [9:1].

Chromatography:

1. Transfer 10.0 ml of a mixture of benzene:ethyl acetate [9:1] to the chromatographic tank. Place a Whatman filter paper disc in the chromatographic tank and close with the lid (for faster saturation of the tank with the solvent system). Allow the tank to saturate for 30 minutes.

2. Apply 5.0 μl of sample(s) and 5.0 μl Standard (as 10.0 mm bands separated by a distance of 15.0 mm, at 10.0 mm from the base) on an HPTLC silica plate using a Linomat HPTLC applicator.

3. Leave the plate in a fume hood to allow the solvent to evaporate. Place the plate in the tank as near vertical as possible, ensuring that the line of application is well above the solvent level. Replace the lid tightly and allow the solvent to ascend to 1.5 cm below the top of the plate.

4. Remove the plate and let it air dry in the fume hood.

Detection: After spraying vanillin-sulphuric acid [white light].

Figure 4:
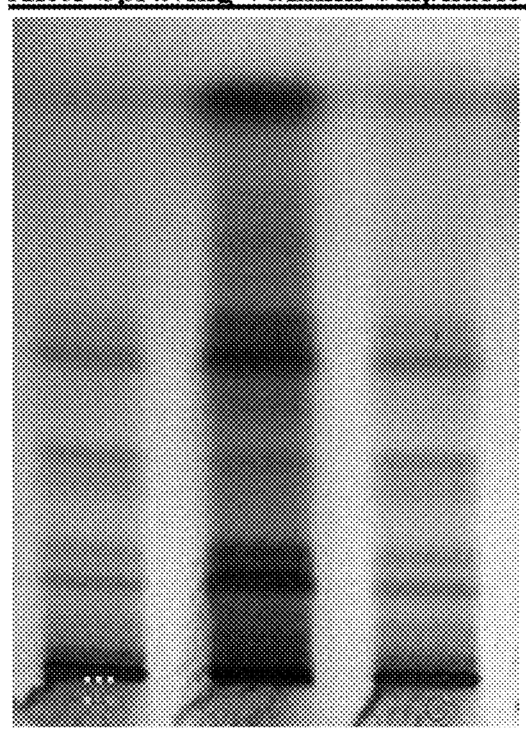
FIG. 4 illustrates an identification of zinzirols in an herbal composition by HPTLC fingerprinting.

Conclusion: As illustrated in FIG. 4, HPTLC fingerprinting of a typical batch of Composition A [KLF/20001] matches with Composition A working standard [KLF/WS/01]. Bands observed in Composition A [KLF/20001] are present in the *Zingiber officinale* (ginger) extract working standard containing zinzirols. These findings confirm that Composition A [KLF/20001] contains zinzirols.

Turnitrates

A *Brassica rapa* (turnip) extract contains turnitrates. The presence of turnitrates in Composition A is confirmed by HPTLC. Details are given below.

Instrument: CAMAG High Performance Thin Layer Chromatography System (HPTLC) comprising: Applicator—Linomat 5, Digistore—2, Multiwavelength Scanner, Transparent Chromatographic Tank, and HPTLC pre-coated silica plate, Silica Gel 60 F254, 10.0×10.0 cm (Merck).

Working Standard Preparation A: 500.0 mg of Composition A working standard [KLF/WS/01] is dissolved in 30.0 ml 95% methanol for 30 minutes in a water bath at 70-80° C. Filter and concentrate to 5.0 ml. Proceed for spotting.

Working Standard Preparation B: 300.0 mg of *Brassica rapa* (turnip) extract working standard [TURP/WS/15] (prepared using botanically authenticated *Brassica rapa* roots) is dissolved in 30.0 ml 95% methanol for 30 minutes in a water bath at 70-80° C. Filter and concentrate to 5.0 ml. Proceed for spotting.

Sample Preparation C: 500.0 mg of a typical batch of Composition A [KLF/20001] is dissolved in 30.0 ml 95% methanol for 30 minutes in a water bath at 70-80° C. Filter and concentrate to 5.0 ml. Proceed for spotting.

Mobile Phase:

Ethylacetate:acetic acid:formic acid:water [10:0.9:0.9:2].

Chromatography:

1. Transfer 10.0 ml of a mixture of ethylacetate:acetic acid:formic acid:water [10:0.9:0.9:2] to the chromatographic tank. Place a Whatman filter paper disc in the chromatographic tank and close with the lid (for faster saturation of the tank with the solvent system). Allow the tank to saturate for 30 minutes.

2. Apply 5.0 μl of sample(s) and 5.0 μl Standard (as 10.0 mm bands separated by a distance of 15.0 mm, at 10.0 mm from the base) on an HPTLC silica plate using a Linomat HPTLC applicator.

3. Leave the plate in a fume hood to allow the solvent to evaporate. Place the plate in the tank as near vertical as possible, ensuring that the line of application is well above the solvent level. Replace the lid tightly and allow the solvent to ascend to 1.5 cm below the top of the plate.

4. Remove the plate and let it air dry in the fume hood.

Detection: After spraying natural product reagent [UV366 nm].

Figure 5:
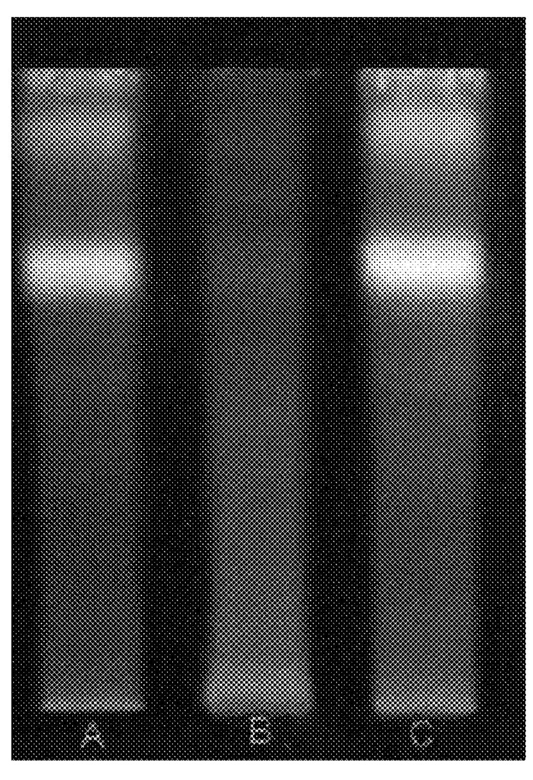
FIG. 5 illustrates an identification of turnitrates in an herbal composition by HPTLC fingerprinting.

Conclusion: As illustrated in FIG. 5, HPTLC fingerprinting of a typical batch of Composition A [KLF/20001] matches with Composition A working standard [KLF/WS/01]. Bands observed in Composition A [KLF/20001] are present in the *Brassica rapa* (ginger) working standard containing turnitrates. These findings confirm that Composition A [KLF/20001] contains turnitrates.

Bitters

A *Momordica charantia* extract contains bitters. The presence of bitters in Composition A is confirmed by HPTLC. Details are given below.

Instrument: CAMAG High Performance Thin Layer Chromatography System (HPTLC) comprising: Applicator—Linomat 5, Digistore—2, Multiwavelength Scanner, Transparent Chromatographic Tank, and HPTLC pre-coated silica plate, Silica Gel 60 F254, 10.0×10.0 cm (Merck).

Working Standard Preparation A: 500.0 mg of Composition A working standard [KLF/WS/01] is dissolved in 30.0 ml 95% methanol for 30 minutes in a water bath at 70-80° C. Filter and concentrate to 5.0 ml. Proceed for spotting.

Working Standard Preparation B: 300.0 mg of *Momordica charantia* working standard [MCE/WS/17] (prepared by using botanically authenticated *Momordica charantia* fruits)

is dissolved in 30.0 ml 95% methanol for 30 minutes in a water bath at 70-80° C. Filter and concentrate to 5.0 ml. Proceed for spotting.

Sample Preparation C: 500.0 mg of a typical batch of Composition A [KLF/20001] is dissolved in 30.0 ml 95% methanol for 30 minutes in a water bath at 70-80° C. Filter and concentrate to 5.0 ml. Proceed for spotting.

Mobile Phase:

Cyclohexane:diethylether:acetic acid [6:4:1].

Chromatography:

1. Transfer 10.0 ml of a mixture of cyclohexane:diethyl ether:acetic acid [6:4:1] to the chromatographic tank. Place a Whatman filter paper disc in the chromatographic tank and close with the lid (for faster saturation of the tank with the solvent system). Allow the tank to saturate for 30 minutes.

2. Apply 5.0 μl of sample(s) and 5.0 μl Standard (as 10.0 mm bands separated by a distance of 15.0 mm, at 10.0 mm from the base) on an HPTLC silica plate using a Linomat HPTLC applicator.

3. Leave the plate in a fume hood to allow the solvent to evaporate. Place the plate in the tank as near vertical as possible, ensuring that the line of application is well above the solvent level. Replace the lid tightly and allow the solvent to ascend to 1.5 cm below the top of the plate.

4. Remove the plate and let it air dry in the fume hood.

Detection: After spraying anisaldehyde sulphuric acid reagent [white light].

Figure 6:
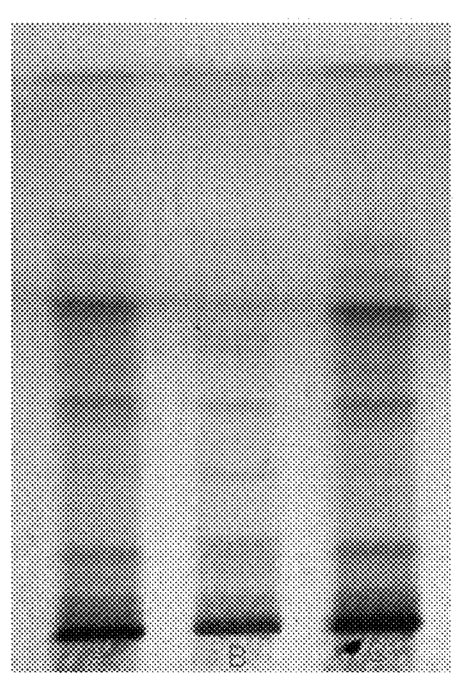
FIG. 6 illustrates an identification of bitters in an herbal composition by HPTLC fingerprinting.

Conclusion: As illustrated in FIG. 6, HPTLC fingerprinting of a typical batch of Composition A [KLF/20001] matches with Composition A working standard [KLF/WS/01]. Bands observed in Composition A [KLF/20001] are present in the *Momordica charantia* extract working standard containing bitters. These findings confirm that Composition A [KLF/20001] contains bitters.

Saponins

An *Asparagus racemosus* extract contains saponins. The presence of saponins in Composition A is confirmed by HPTLC. Details are given below.

Instrument: CAMAG High Performance Thin Layer Chromatography System (HPTLC) comprising: Applicator—Linomat 5, Digistore—2, Multiwavelength Scanner, Transparent Chromatographic Tank, and HPTLC pre-coated silica plate, Silica Gel 60 F254, 10.0×10.0 cm (Merck).

Working Standard Preparation A: 500.0 mg of Composition A working standard [KLF/WS/01] is dissolved in 30.0 ml 95% methanol for 30 minutes in a water bath at 70-80° C. Filter and concentrate to 5.0 ml. Proceed for spotting.

Working Standard Preparation B: 300.0 mg of *Asparagus racemosus* extract working standard [ARE/WS/17] (prepared using botanically authenticated *Asparagus racemosus* roots) is dissolved in 30.0 ml 95% methanol for 30 minutes in a water bath at 70-80° C. Filter and concentrate to 5.0 ml. Proceed for spotting.

Sample Preparation C: 500.0 mg of a typical batch of Composition A [KLF/20001] is dissolved in 30.0 ml 95% methanol for 30 minutes in a water bath at 70-80° C. Filter and concentrate to 5.0 ml. Proceed for spotting.

Mobile Phase:

Chloroform:acetic acid:methanol:water [6:3.2:1.2:0.8].

Chromatography:

1. Transfer 10.0 ml of a mixture of chloroform:acetic acid:methanol:water [6:3.2:1.2:0.8] to the chromatographic tank. Place a Whatman filter paper disc in the chromatographic tank and close with the lid (for faster saturation of the tank with the solvent system). Allow the tank to saturate for 30 minutes.

2. Apply 5.0 μl of sample(s) and 5.0 μl Standard (as 10.0 mm bands separated by a distance of 15.0 mm, at 10.0 mm from the base) on an HPTLC silica plate using a Linomat HPTLC applicator.

3. Leave the plate in a fume hood to allow the solvent to evaporate. Place the plate in the tank as near vertical as possible, ensuring that the line of application is well above the solvent level. Replace the lid tightly and allow the solvent to ascend to 1.5 cm below the top of the plate.

4. Remove the plate and let it air dry in the fume hood.

Detection: After spraying vanillin-sulphuric acid [UV 366 nm] and spraying vanillin-sulphuric acid [white light].

Figure 7:
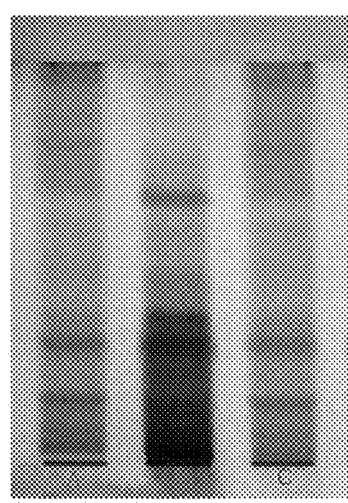
FIG. 7 illustrates an identification of saponins in an herbal composition by HPTLC fingerprinting.

Conclusion: As illustrated in FIG. 7, HPTLC fingerprinting of a typical batch of Composition A [KLF/20001] matches with Composition A working standard [KLF/WS/01]. Bands observed in Composition A [KLF/20001] are present in the *Asparagus racemosus* extract working standard containing saponins. These findings confirm that Composition A [KLF/20001] contains saponins.

Tannins

A *Phyllanthus niruri* extract contains tannins. The presence of tannins in Composition A is confirmed by HPTLC. Details are given below.

Instrument: CAMAG High Performance Thin Layer Chromatography System (HPTLC) comprising: Applicator—Linomat 5, Digistore—2, Multiwavelength Scanner, Transparent Chromatographic Tank, and HPTLC pre-coated silica plate, Silica Gel 60 F254, 10.0×10.0 cm (Merck).

Working Standard Preparation A: 500.0 mg of Composition A working standard [KLF/WS/01] is dissolved in 30.0 ml 95% methanol for 30 minutes in a water bath at 70-80° C. Filter and concentrate to 5.0 ml. Proceed for spotting.

Working Standard Preparation B: 300.0 mg of *Phyllanthus niruri* extract working standard [PHY/WS/16] (prepared using botanically authenticated *Phyllanthus niruri* aerial parts) is dissolved in 30.0 ml 95% methanol for 30 minutes in a water bath at 70-80° C. Filter and concentrate to 5.0 ml. Proceed for spotting.

Sample Preparation C: 500.0 mg of a typical batch of Composition A [KLF/20001] is dissolved in 30.0 ml 95% methanol for 30 minutes in a water bath at 70-80° C. Filter and concentrate to 5.0 ml. Proceed for spotting.

Mobile Phase:

Chloroform:methanol:formicacid:acetic acid [8.5:1.5:0.9:0.9].

Chromatography:

1. Transfer 10.0 ml of a mixture of chloroform:methanol:formic acid:acetic acid [8.5:1.5:0.9:0.9] to the chromatographic tank. Place a Whatman filter paper disc in the chromatographic tank and close with the lid (for faster saturation of the tank with the solvent system). Allow the tank to saturate for 30 minutes.

2. Apply 5.0 μl of sample(s) and 5.0 μl Standard (as 10.0 mm bands separated by a distance of 15.0 mm, at 10.0 mm from the base) on an HPTLC silica plate using a Linomat HPTLC applicator.

3. Leave the plate in a fume hood to allow the solvent to evaporate. Place the plate in the tank as near vertical as possible, ensuring that the line of application is well above the solvent level. Replace the lid tightly and allow the solvent to ascend to 1.5 cm below the top of the plate.

4. Remove the plate and let it air dry in the fume hood.

Detection: After spraying natural product reagent [UV366 nm] and after spraying natural product reagent+PEG [UV366 nm].

Figure 8:
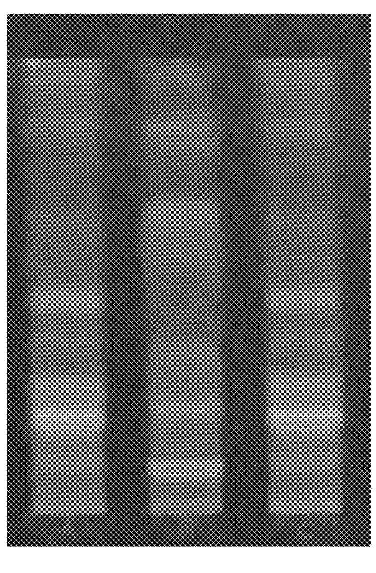
FIG. 8 illustrates an identification of tannins in an herbal composition by HPTLC fingerprinting.
Figure 8:
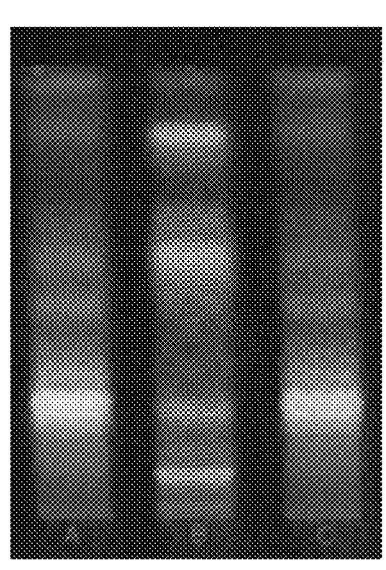

Conclusion:

As illustrated in FIG. 8, HPTLC fingerprinting of a typical batch of Composition A [KLF/20001] matches with Composition A working standard [KLF/WS/01]. Bands observed in Composition A [KLF/20001] are present in the *Phyllanthus niruri* extract working standard containing tannins. These findings confirm that Composition A [KLF/20001] contains tannins.

Example 4: In Vivo Studies in Human Subjects

Composition A from Example 2 was prepared and sent for in vivo study. The study is a randomized, double-blind, parallel, placebo-controlled study. FIG. 1 illustrates the study design. Composition A and placebo were separately encapsulated. The Composition A capsule contained 500.0 mg of Composition A. The daily dosage was 2 capsules per day in the clinical trial, which makes the daily dosage 1.0 g. The placebo capsule was filled with only nonactive ingredients.

Patients and Sample Size

Adult male or female subjects between 18 to 70 years old were recruited for this study. Subjects were screened for study eligibility.

A total of 66 subjects were screened for the inclusion and exclusion criteria at the initial visit. Of those screened, 60 subjects were eligible to participate and signed the informed consent. Thirty subjects were randomized in each treatment arm. One subject from the placebo arm dropped out due to personal reasons.

Eligibility criteria included: (a) adults aged between 18 to 70 years with mild to moderately elevated liver enzyme levels based on medical history, physical examination, and laboratory tests (these subjects were otherwise healthy); (b) subjects who could provide written informed consent, and were able to understand and willing to comply with the requirements of the study; (c) subjects with alanine aminotransferase (ALT) and aspartate aminotransferase (AST) ≥1.5 times the upper limit of normal; and (d) subjects with a ratio of AST to ALT>1.5.

Exclusion criteria for this study included: (a) pregnant women and women of childbearing potential who were at risk of pregnancy; (b) subjects with severe alcoholic hepatitis who had cirrhosis or a life expectancy less than three months; (c) subjects with severe renal impairment defined by a glomerular filtration rate below 60.0 ml/min per 1.73 $m^2$; (d) subjects with hepatic disorders due to cardiac causes, inherited metabolic causes, hemochromatosis, or Wilson's disease; (e) subjects with severe alcoholic hepatitis with cirrhosis; (f) subjects with active viral hepatitis; (g) subjects undergoing active treatment for alcohol withdrawal syndrome at study entry; (h) subjects on hepatotoxic medications, such as antitubercular medication, antiviral medication, paracetamol, etc.; (i) subjects participating in another clinical trial with an active intervention, drug, or device with the last dose taken within 60 days; (j) subjects with any other condition which, in the opinion of the investigator, would adversely affect the subject's ability to complete the study or its measures; and (k) subjects who had a known allergy to the ingredients present in Composition A.

Patients not meeting the inclusion criteria or meeting the exclusion criteria at the time of screening were not included in the analysis. Eligible subjects were allowed to withdraw from the study at any time.

Trial Design

Eligible subjects who completed informed consent were randomly allocated to the treatment groups (Composition A or placebo). Randomization of participants was performed through computer-generated randomization codes using permuted block design and the selections were known only to the statistician until the analysis was completed. Allocation concealment was done using sequentially numbered opaque sealed envelopes; everyone involved in the study, except for the statistician, was blinded to medication assignments. Thirty subjects were allocated to each group with a total of 60 participants: Group A (n=30 subjects), Investigation Product (IP) Composition A; and Group B (n=30 subjects), placebo. Duration of study was 56 days with four scheduled visits (screening visits, randomization visits, day 1, day 28, and day 56). Each visit had a flexibility window of ±two days.

Study medications were packed according to an assigned randomization number. Sealed packs of Composition A were provided to the clinical site. Either Composition A or placebo was dispensed to the subjects on Visit 2 (day 1) and Visit 3 (day 28). Composition A or placebo capsules were taken orally twice daily half an hour after breakfast and half an hour after dinner, respectively, for 56 days.

Each subject underwent clinical laboratory tests at screening visits and at follow-up visits. Urine, for urinalysis, and blood, for hematology and biochemistry, were collected during screening visits and at the end of the study visits. Blood samples were collected by direct venipuncture for hematology, biochemistry, and serology laboratory tests.

Compliance and Adverse Events (AEs)

At each visit, excess medication was returned to investigators to confirm that the correct number of capsules had been taken. AEs (if any) were recorded. Information collected included the nature, date and time of onset, intensity, duration, causality, action taken, and outcome of the event. Details of medications given to the subject (to abate the AEs) were recorded on the concomitant medication page by the investigator.

All AEs during the study were followed until resolution (returned to normal or baseline values), stabilization, or until judged to be no longer clinically significant by investigators. Since all AEs were mild to moderate in nature, no supplemental measurements and no evaluations (such as laboratory tests, diagnostic procedures, or consultation with other healthcare professionals) were necessary to investigate the nature and/or causality of an AE. There were no serious adverse events (SAEs) reported. The minor adverse events were evenly distributed in the Composition A and placebo groups. These minor adverse events were self-limiting and subsided with use of concomitant medication or without any intervention. Thus, Composition A is safe for human consumption.

Withdrawal and Dropout

Subjects who did not meet the inclusion/exclusion criteria were considered screening failures. Participating subjects could withdraw from the study at any time without justification of his/her decision, even after undergoing consent. No subjects were discontinued due to noncompliance with medication, protocol violation, worsening of disease or tolerability, AEs, or SAEs. One subject in Group B (placebo group) dropped out from the study due to personal reasons and not due to any AE.

Primary Outcome Measures

Sample size was calculated using repeated measure analysis of covariance, keeping aspartate aminotransferase, also known as serum glutamic oxaloacetic transaminase (AST/SGOT), alanine aminotransferase (formerly called serum glutamic pyruvic transaminase (ALT/SGPT)), alkaline phosphatase (ALP), and total serum bilirubin as primary objectives. An anticipated standardized effect size of 0.4 and interclass correlation of 0.6 was assumed. Considering a dropout rate of 15%, 30 subjects were recruited in each arm to obtain a power of more than 80% to meet the primary objective.

ALT/SGPT: ALT/SGPT helps with protein metabolism. When the liver is impaired, ALT can leak into the blood. Normal levels of ALT are below 45 IU/L in males, while these levels are somewhat lower in females and vary depending on age.

AST/SGOT: AST is an enzyme found in many parts of the body, including the heart, liver, muscles, and kidney. AST gets released into the blood when there is damage to any of the organs where it is present. Thus, elevated blood AST levels are not conclusive indicators of liver damage, and AST is measured with ALT to make a more liver-specific diagnosis. Normal levels of AST are under 35 IU/L in adults.

ALP: ALP is an enzyme mainly found in the liver but can also be found in other parts of the body, such as bones and bile ducts. ALP gets released into the blood when there is damage to any part of the body containing ALP. Liver impairment, obstructed bile ducts, and bone-related problems can all lead to raised ALP levels in the blood. Normal levels of ALP are between 30 and 120 IU/L.

Total Serum Bilirubin: When red blood cells (RBCs) are broken down, a waste product called bilirubin is generated. When the liver is damaged, bilirubin cannot be cleared as effectively leading to elevated bilirubin levels in the blood. The normal range of serum bilirubin is 2 to 17 micromoles/L (0.12-1.0 mg/dL).

Secondary Outcome Measures

Change in Quality of Life (QOL) scores were measured for physical and psychosocial health. Also, safety and tolerability were assessed during the clinical trial. Changes from baseline to the end of the study period in these parameters were monitored to determine the overall safety and tolerability of Composition A: malondialdehyde (MDA), superoxide dismutase (SOD), and gamma-glutamyl transferase (GGT).

QOL: QOL was assessed through a pre- and post-questionnaire short form (SF) 36. The questionnaire had eight domains: physical functioning, limitations due to physical health, limitations due to emotional problems, energy/fatigue, emotional well-being, social functioning, pain, and general health. All covariate factors were adjusted to find the exact influence of liver disease on the domains. Higher scores for each domain indicate improvement in the QOL.

MDA: Lipid peroxidation is a chain of reactions in hepatocytes leading to oxidative stress and the formation of a toxic product called MDA. Higher values of MDA indicate oxidative stress.

SOD: SOD protects cells from oxidative stress and the toxic effects of endogenously generated superoxide radicals (free radicals). Disturbances in the antioxidant system (which neutralizes free radicals) may play a role in the pathogenesis of chronic liver disease. The release of reactive oxygen species occurs when products of free radical reactions are involved in pathogenesis and/or progression of medical cholestasis. When free radicals are released, the serum SOD increases to minimize the liver injury. Hence, low levels of SOD may lead to more liver damage.

GGT: GGT is an enzyme found in high levels in the liver. Elevated serum GGT is a sign that the liver or bile ducts are impaired.

Statistical Analysis

Data collected from the study site were assessed using the Statistical Package for Social Sciences (SPSS) software, version 21, SPSS Inc., Chicago, Il., USA. Significance was defined as a p value<0.05. Descriptive analysis for baseline summary statistics including mean, median, standard deviation for demographic data, and proportion of males and females were completed. Inferential statistics were performed with one-way analyses of variance (ANOVAs) with Tukey tests for primary outcome and biomarkers intragroup comparison. Paired student t-tests were performed to analyze safety data. Unpaired student t-tests were performed for intergroup comparison. Missing observations were imputed using the last observation carried forward approach.

Results

Of the 66 subjects who participated in the screening visit, six were screening failures. Sixty subjects qualified for the study based on the inclusion/exclusion criteria, and all signed the informed consent. Subjects were randomized to groups: Group A received Composition A, and Group B received the placebo. One subject dropped out of the study from Group B due to personal reasons. The final statistical analyses and results were depicted for 59 participants at the end of the study.

A summary of baseline demographic data of included subjects meeting the eligibility criteria and providing signed informed consent is shown in Tables 1 and 2.

TABLE 1

| Variable | Statistics | Group A and B (N = 60) |
|---|---|---|
| Height at baseline (cm) | Mean (SD) | 159.13 (8.14) |
| | (Min, Max) | (143, 175) |
| Weight at baseline (kg) | Mean (SD) | 58.50 (8.17) |
| | (Min, Max) | (41, 79) |
| BMI at baseline ($kg/m^2$) | Mean (SD) | 23.12 (2.33) |
| | (Min, Max) | (19.30, 28.70) |

TABLE 2

| Variable | Statistics | Group A (N = 30) | Group B (N = 30) |
|---|---|---|---|
| Gender | | | |
| Male | N (%) | 16 (53.3%) | 17 (56.7%) |
| Female | N (%) | 14 (46.7%) | 13 (43.3%) |
| Age at baseline | Mean (SD) | 40.666 (12.56) | 38.57 (10.22) |
| | (Min, Max) | (19, 68) | (20, 64) |

Table 3 depicts vital signs of the participants at each visit.

TABLE 3

| Visit | | Pulse Rate (bpm) | Respiratory Rate | Temperature (° F.) | Systolic Blood Pressure (mmHg) | Diastolic Blood Pressure (mmHg) |
|---|---|---|---|---|---|---|
| Visit 1 | Mean | 75.17 | 16.10 | 98.26 | 121.63 | 79.60 |
| | N | 60 | 60 | 60 | 60 | 60 |
| (Baseline) | SD | 7.26 | 1.41 | 0.61 | 8.6 | 5.75 |
| Visit 2 | Mean | 75.27 | 16.08 | 98.31 | 121.67 | 78.55 |
| | N | 60 | 60 | 60 | 60 | 60 |
| | SD | 8.15 | 1.42 | 0.55 | 6.91 | 5.1 |
| Visit 3 | Mean | 74.08 | 16.05 | 98.32 | 120.95 | 78.65 |
| | N | 60 | 60 | 60 | 60 | 60 |
| | SD | 7.065 | 1.42 | 0.6 | 6.81 | 5.21 |
| Visit 4 | Mean | 73.97 | 16.10 | 98.27 | 122.03 | 78.72 |
| (End of | N | 59 | 59 | 59 | 59 | 59 |
| the | SD | 6.37 | 1.46 | 0.49 | 7.39 | 5.03 |
| study) | p value | .651 | .997 | .920 | .882 | .677 |

Table 4 shows a statistical summary of primary outcomes at different visits. * refers to a p value<0.05. As shown in Table 4, changes in levels of ALT/SGPT, AST/SGOT, bilirubin, and ALP levels were measured at baseline, 28 days (Visit 3), and at the end of the study (56 days).

TABLE 4

| Variable | Baseline | Subsequent Visits | Mean Difference (Visit 1 − Subsequent Visit) | P Value Difference |
|---|---|---|---|---|
| Group A - Composition A | | | | |
| ALT/SGPT (IU/L) | Visit 1 (Baseline) | Visit 3 | 17.50000 | <.001* |
| | | Visit 4 (End of the study) | 31.93333 | <.001* |
| AST/SGOT (IU/L) | Visit 1 (Baseline) | Visit 3 | 29.13333 | <.001* |
| | | Visit 4 (End of the study) | 65.23333 | <.001* |
| Bilirubin (mg/dL) | Visit 1 (Baseline) | Visit 3 | 0.15167 | <.001* |
| | | Visit 4 (End of the study) | 0.24833 | <.001* |
| ALP (IU/L) | Visit 1 (Baseline) | Visit 3 | 14.43333 | <.001* |
| | | Visit 4 (End of the study) | 25.03333 | <.001* |
| Group B - Placebo | | | | |
| ALT/SGPT (IU/L) | Visit 1 (Baseline) | Visit 3 | 10.56782 | <.001* |
| | | Visit 4 (End of the study) | 14.91264 | <.001* |
| AST/SGOT (IU/L) | Visit 1 (Baseline) | Visit 3 | 17.22299 | <.001* |
| | | Visit 4 (End of the study) | 29.01609 | <.001* |
| Bilirubin (mg/dl) | Visit 1 (Baseline) | Visit 3 | 0.08933 | .001* |
| | | Visit 4 (End of the study) | 0.15092 | <.001* |
| ALP (IU/L) | Visit 1 (Baseline) | Visit 3 | 8.02414 | .006* |
| | | Visit 4 (End of the study) | 11.85172 | <.001* |

Tables 5(a)-(c) show intergroup comparisons of primary outcomes (Group A (Composition A) versus Group B (placebo)). * refers to a p value<0.05. As shown in Table 5(a), analysis between the groups at Visit 1 (baseline) for all primary outcomes showed no statistical differences between the two groups (p value>0.05).

TABLE 5(a)

| Visit 1 (Baseline) | | | | | |
|---|---|---|---|---|---|
| Tests | Group | Mean | Standard Deviation | Mean Difference (Group A − Group B) | P Value |
| ALT/SGPT Visit 1 (Baseline) (IU/L) | Group A | 79.1333 | 7.51887 | 2.60000 | 0.155 |
| | Group B | 76.5333 | 6.43125 | | |
| AST/SGOT Visit 1 (Baseline) (IU/L) | Group A | 122.4000 | 11.77256 | 2.86667 | 0.307 |
| | Group B | 119.5333 | 9.66948 | | |
| Bilirubin Visit 1 (Baseline) (mg/dl) | Group A | 1.2183 | 0.13269 | 0.01500 | 0.650 |
| | Group B | 1.2033 | 0.12215 | | |
| Alkaline phosphatase Visit 1 (Baseline) (IU/L) | Group A | 119.7333 | 15.24950 | 2.43333 | 0.504 |
| | Group B | 117.3000 | 12.62769 | | |

As shown in Table 5(b), at Visit 3, there was a statistically significant difference between the two groups for ALT/SGPT, AST/SGOT, and bilirubin (p value<0.05).

TABLE 5(b)

| Visit 3 (Day 28) | | | | | |
|---|---|---|---|---|---|
| | Visit 3 (Day 28) | | | | |
| Test | Group | Mean | Standard Deviation | Mean Difference (Group A − Group B) | P Value |
| ALT/SGPT Visit 3 (IU/L) | Group A | 61.6333 | 7.21819 | −4.33218 | 0.01 |
| | Group B | 65.9655 | 5.29476 | | |
| AST/SGOT Visit 3 (IU/L) | Group A | 93.2667 | 9.26221 | −9.04368 | <0.001* |
| | Group B | 102.3103 | 8.56114 | | |
| Bilirubin Visit 3 (mg/dl) | Group A | 1.0667 | 0.09911 | −0.04733 | 0.050* |
| | Group B | 1.1140 | 0.08115 | | |
| Alkaline phosphatase Visit 3 (IU/L) | Group A | 105.3000 | 9.34455 | −3.97586 | 0.102 |
| | Group B | 109.2759 | 9.02733 | | |

As shown in Table 5(c), at Visit 4, there was a statistically significant difference between the two groups for all primary parameters (p value<0.05), showing that Composition A was significantly more effective than the placebo for all primary outcomes.

TABLE 5(c)

| Visit 4 (Day 56) | | | | | |
|---|---|---|---|---|---|
| | Visit 4 | | | | |
| Test | Group | Mean | Standard Deviation | Mean Difference (Group A − Group B) | P Value |
| ALT/SGPT Visit 4 (End of the study) (IU/L) | Group A | 47.2000 | 5.08141 | −14.42069 | <0.001* |
| | Group B | 61.6207 | 4.27963 | | |
| AST/SGOT Visit 4 (End of the study) (IU/L) | Group A | 57.1667 | 8.51807 | −33.35057 | <0.001* |
| | Group B | 90.5172 | 8.65044 | | |
| Bilirubin Visit 4 (End of the study) (mg/dl) | Group A | 0.9700 | 0.07506 | −0.08241 | <0.001* |
| | Group B | 1.0524 | 0.05604 | | |
| Alkaline phosphatase Visit 4 (End of the study) (IU/L) | Group A | 94.7000 | 8.07785 | −10.74828 | <0.001* |
| | Group B | 105.4483 | 6.02724 | | |

Table 6 shows an intergroup comparison of primary outcomes between Group A (Composition A) and Group B (placebo). * refers to a p value<0.05.

As shown in Table 6, there was a reduction in ALT/SGPT from a mean of 79.13 (baseline) to 61.63 (day 28) to 47.20 (day 56) in the Composition A group, resulting in a 40.35% reduction from baseline to the end of the study. The placebo group showed a reduction of mean ALT/SGPT from 76.53

(baseline) to 65.97 (day 28) to 61.62 (day 56), totaling a 19.48% reduction from baseline to the end of the study.

As shown in Table 6, there was a reduction in AST/SGOT in the Composition A group from a mean of 122.40 (baseline) to 93.27 (day 28) to 57.17 (day 56), totaling a 53.3% reduction from baseline to the end of the study. The placebo group had a reduction of mean AST/SGOT from 119.53 (baseline) to 102.31 (day 28) to 90.52 (day 56), totaling a 24.28% reduction from baseline to the end of the study.

As shown in Table 6, there was a reduction of mean bilirubin in the Composition A group from 1.22 (baseline) to 1.07 (day 28) to 0.97 (day 56), resulting in a 20.38% reduction from baseline to the end of the study. In the placebo group, there was a reduction of mean bilirubin from 1.20 (baseline) to 1.11 (day 28) to 1.05 (day 56), resulting in a 12.54% reduction from baseline to the end of the study.

As shown in Table 6, there was a reduction of mean alkaline phosphatase (ALP) in the Composition A group from 119.73 (baseline) to 105.30 (day 28) to 94.70 (day 56), totaling in a 20.67% reduction from baseline to the end of the study. There was a decrease in mean ALP in the placebo group from 117.30 (baseline) to 109.28 (day 28) to 105.45 (day 56), resulting in a 10.11% reduction from baseline to the end of the study.

TABLE 6

| | Group A | | | Group B | | |
|---|---|---|---|---|---|---|
| Measures | Visit 1 | Visit 3 (Day 28) | Visit 4 (Day 56) | Visit 1 | Visit 3 (Day 28) | Visit 4 (Day 56) |
| ALT/SGPT (IU/L) | 79.13 (7.52) | 61.63 (7.22) | 47.20 (5.08) | 76.53 (6.43) | 65.97 (5.29) | 61.62 (4.28) |
| AST/SGOT (IU/L) | 122.40 (11.77) | 93.27 (9.26) | 57.17 (8.52) | 119.53 (9.67) | 102.31 (8.56) | 90.52 (8.65) |
| Bilirubin (mg/dl) | 1.22 (0.13) | 1.07 (0.1) | 0.97 (0.08) | 1.20 (0.12) | 1.11 (0.08) | 1.05 (0.06) |
| ALP (IU/L) | 119.73 (15.25) | 105.30 (9.34) | 94.70 (8.08) | 117.30 (12.63) | 109.28 (9.03) | 105.45 (6.03) |

Analysis of Secondary Outcomes

Malondialdehyde (MDA)

Table 7 summarizes biomarkers in Group A (Composition A group). * refers to a p value<0.05. As shown in Table 7, in the Composition A group, mean MDA levels decreased from 3.44±0.43 at baseline to 2.51±0.37 at the end of the study.

TABLE 7

| | Test | Mean | Standard Deviation | Mean Difference (Visit 1 − Visit 4) | P Value |
|---|---|---|---|---|---|
| MDA (μmol/l) | Visit 1 (Baseline) | 3437 | .433 | 0.925 | <0.001* |
| | Visit 4 (End of the study) | 2.512 | .367 | | |
| SOD (U/ml) | Visit 1 (Baseline) | 179.967 | 13.718 | −36.167 | <0.001* |
| | Visit 4 (End of the study) | 216.133 | 20.844 | | |
| GGT (U/L) | Visit 1 (Baseline) | 69.033 | 11.637 | 14.600 | <0.001* |
| | Visit 4 (End of the study) | 54.433 | 10.592 | | |

Table 8 summarizes biomarkers in Group B (placebo group). * refers to a p value<0.05. As shown in Table 8, in the placebo group, mean MDA levels decreased from 3.33±0.58 at baseline to 3.31±0.5 at the end of the study.

TABLE 8

| | Test | Mean | Standard Deviation | Mean Difference (Visit 1 − Visit 4) | P Value |
|---|---|---|---|---|---|
| MDA (μmol/l) | Visit 1 (Baseline) | 3.331 | 0.578 | 0.019 | 0.715 |
| | Visit 4 (End of the study) | 3.312 | 0.498 | | |
| SOD (U/ml) | Visit 1 (Baseline) | 205.759 | 26.235 | −1.758 | 0.253 |
| | Visit 4 (End of the study) | 207.517 | 27.865 | | |
| GGT (U/L) | Visit 1 (Baseline) | 66.517 | 11.642 | 3.034 | 0.007* |
| | Visit 4 (End of the study) | 63.483 | 13.325 | | |

Table 9 shows an intergroup comparison between the groups using an independent t-test at Visit 1 and Visit 4. * refers to a p value<0.05. As shown in Table 9, Composition A resulted in a statistically significant decrease in MDA levels when compared to the placebo (p value<0.05).

TABLE 9

| | | Mean | Std. Deviation | Mean Diff. (Group A − Group B) | P Value |
|---|---|---|---|---|---|
| MDA Visit 1 (Baseline) (μmol/l) | Group A | 3.4370 | .43338 | 0.10631 | 0.084 |
| | Group B | 3.3307 | .57775 | | |
| MDA Visit 4 (End of the study) (μmol/l) | Group A | 2.5123 | .36705 | −0.80008 | 0.026* |
| | Group B | 3.3124 | .49809 | | |
| SOD Visit 1 (Baseline) (U/ml) | Group A | 179.9667 | 13.71755 | −25.79195 | 0.000* |
| | Group B | 205.7586 | 26.23473 | | |
| SOD Visit 4 (End of the study) (U/ml) | Group A | 216.1333 | 20.84381 | 8.61609 | 0.072 |
| | Group B | 207.5172 | 27.86526 | | |
| GGT Visit 1 (Baseline) (U/L) | Group A | 69.0333 | 11.63669 | 2.51609 | 0.887 |
| | Group B | 66.5172 | 11.64235 | | |
| GGT Visit 4 (End of the study) (U/L) | Group A | 54.4333 | 10.59174 | −9.04943 | 0.313 |
| | Group B | 63.4828 | 13.32458 | | |

Superoxide Dismutase (SOD)

As shown in Table 7, mean SOD levels in Group A were significantly increased from baseline (179.97±13.72) to the end of the study (216.13±20.84) (p value<0.05). As shown in Table 8, for Group B, the baseline and end of the study values were 205.76±26.23 and 207.52±27.87, respectively, but this change was not statistically significant.

Gamma-Glutamyl Transferase (GGT)

As shown in Table 7, mean GGT levels in Group A at baseline and the end of study were 69.03±11.64 and 54.43±10.59, respectively. As shown in Table 8, mean GGT in Group B was 66.52±11.64 at baseline and 63.48±13.32 at the end of the study. Both Groups A and B had a statistically significant decrease in mean GGT levels from baseline to the end of study (p value<0.05).

As shown in Table 7, overall, the treatment group exhibited a statistically significant decrease in MDA and/or GGT levels from baseline to the end of the study while the SOD levels exhibited a statistically significant increase. As shown in Table 8, the placebo group exhibited a statistically significant decrease in GGT levels from baseline to the end of the study. In contrast, there was no statistically significant change observed in MDA and/or SOD for the placebo group.

Analysis of QOL

The QOL parameters were assessed for Groups A and B. Table 10 shows QOL parameters assessed using SF 36 at Visit 1 and Visit 4 for both Group A and Group B. * refers to a p value<0.05. Patients in Group A exhibited significant improvement in all the parameters from Visit 1 to Visit 4, whereas in Group B, except for the physical functioning parameter, there was no meaningful change seen from baseline to Visit 4. At baseline, there was no statistically significant difference between the groups in any parameter (P>0.05). However, by the end of the study (Visit 4), there was a statistically significant difference between Groups A and B in all parameters (p value<0.05).

TABLE 10

| | | VISIT 1 | | | VISIT 4 | | |
|---|---|---|---|---|---|---|---|
| | | Mean | Standard Deviation | P Value (Group A − Group B) | Mean | Standard Deviation | P Value (Group A − Group B) |
| Physical functioning | Group A | 26.72 | 31.42 | 0.167 | 69.83 | 26.78 | <.001* |
| | Group B | 25 | 27.67 | | 35.67 | 26.56 | |
| Role limitation due to physical health | Group A | 17.50 | 38.16 | 0.435 | 62.93 | 48.51 | <.001* |
| | Group B | 14.17 | 35.02 | | 13.79 | 34.63 | |
| Role limitations due to emotional problems | Group A | 30 | 46.08 | | 100 | 0.00 | <.001* |
| | Group B | 33.33 | 47.40 | 0.567 | 32.18 | 46.99 | |
| Energy/fatigue | Group A | 27.33 | 22.89 | 0.632 | 42.50 | 26.21 | <.001* |
| | Group B | 28.50 | 21.17 | | 27.93 | 20.91 | |
| Emotional well-being | Group A | 32.13 | 21.97 | 0.931 | 52.41 | 21.35 | <.001* |
| | Group B | 31.93 | 23.56 | | 32.00 | 22.41 | |
| Social functioning | Group A | 30.83 | 19.73 | 0.689 | 55.43 | 21.51 | <.001* |
| | Group B | 29.58 | 23.69 | | 27.16 | 24.00 | |
| Pain | Group A | 22 | 15.82 | 0.053 | 33.97 | 21.21 | <.001* |
| | Group B | 17.25 | 13.23 | | 18.19 | 15.12 | |
| General health | Group A | 29.17 | 23.43 | 0.821 | 60.69 | 22.39 | <.001* |
| | Group B | 28.66 | 22.31 | | 26.72 | 21.98 | |

What is claimed is:

1. A composition for supporting, maintaining, or improving liver health comprising:
   - about 15% to about 25% of *Andrographis paniculata* extract;
   - about 5% to about 15% of *Zingiber officinale* extract;
   - about 5% to about 15% of *Brassica rapa* extract;
   - about 25% to about 35% of *Momordica charantia* extract;
   - about 10% to about 20% of *Asparagus racemosus* extract; and
   - about 10% to about 20% of *Phyllanthus niruri* extract; each by weight relative to the total weight of the composition.

2. The composition according to claim 1, wherein the composition comprises:
   - about 18% to about 22% of the *Andrographis paniculata* extract;
   - about 8% to about 12% of the *Zingiber officinale* extract;
   - about 8% to about 12% of the *Brassica rapa* extract;
   - about 28% to about 32% of the *Momordica charantia* extract;
   - about 13% to about 18% of the *Asparagus racemosus* extract; and
   - about 13% to about 18% of the *Phyllanthus niruri* extract.

3. The composition according to claim 1, wherein the composition comprises:
   - about 19% to about 21% of the *Andrographis paniculata* extract;
   - about 9% to about 11% of the *Zingiber officinale* extract;
   - about 9% to about 11% of the *Brassica rapa* extract;
   - about 29% to about 31% of the *Momordica charantia* extract;
   - about 14% to about 16% of the *Asparagus racemosus* extract; and
   - about 14% to about 16% of the *Phyllanthus niruri* extract.

4. The composition according to claim 1, wherein the composition comprises:
   - about 20% of the *Andrographis paniculata* extract;
   - about 10% of the *Zingiber officinale* extract;
   - about 10% of the *Brassica rapa* extract;
   - about 30% of the *Momordica charantia* extract;
   - about 15% of the *Asparagus racemosus* extract; and
   - about 15% of the *Phyllanthus niruri* extract.

5. The composition according to claim 1, wherein the composition comprises no less than 0.5% of livolides, by weight relative to the total weight of the composition.

6. The composition according to claim 1, wherein the composition comprises no less than 1.5% of livolides, by weight relative to the total weight of the composition.

7. The composition according to claim 1, wherein the composition comprises no less than 0.2% of zinzirols, by weight relative to the total weight of the composition.

8. The composition according to claim 1, wherein the composition comprises no less than 0.4% of zinzirols, by weight relative to the total weight of the composition.

9. The composition according to claim 1, wherein the composition comprises no less than 0.1% of turnitrates, by weight relative to the total weight of the composition.

10. The composition according to claim 1, wherein the composition comprises no less than 0.25% of turnitrates, by weight relative to the total weight of the composition.

11. The composition according to claim 1, wherein the composition comprises no less than 2% of saponins, by weight relative to the total weight of the composition.

12. The composition according to claim 1, wherein the composition comprises no less than 1% of bitters, by weight relative to the total weight of the composition.

13. The composition according to claim 1, wherein the composition comprises no less than 1% of tannins, by weight relative to the total weight of the composition.

14. The composition according to claim 1, wherein the composition comprises:
no less than 0.5% of livolides;
no less than 0.2% of zinzirols; and
no less than 0.1% of turnitrates, by weight relative to the total weight of the composition.

15. The composition according to claim 1, wherein the composition comprises:
no less than 1.5% of livolides;
no less than 0.4% of zinzirols; and
no less than 0.25% of turnitrates, by weight relative to the total weight of the composition.

16. The composition according to claim 1, wherein the composition further comprises:
no less than 3% of saponins;
no less than 2% of bitters; and
no less than 2% of tannins, by weight relative to the total weight of the composition.

17. The composition according to claim 16, wherein the composition comprises:
no less than 0.5% of livolides;
no less than 0.2% of zinzirols; and
no less than 0.1% of turnitrates, by weight relative to the total weight of the composition.

18. The composition according to claim 16, wherein the composition comprises:
no less than 1.5% of livolides;
no less than 0.4% of zinzirols; and
no less than 0.25% of turnitrates, by weight relative to the total weight of the composition.

19. The composition according to claim 1, when administered to a subject, results in a reduction of at least 15% alanine aminotransferase (ALT) levels.

20. The composition according to claim 1, when administered to a subject, results in a reduction of at least 20% aspartate aminotransferase (AST) levels.

21. The composition according to claim 1, when administered to a subject, results in a reduction of at least 10% alkaline phosphatase (ALP) levels.

22. The composition according to claim 1, when administered to a subject, results in a reduction of at least 10% bilirubin levels.

23. The composition according to claim 1, when administered to a subject, results in a reduction of at least 25% malondialdehyde (MDA) levels.

24. The composition according to claim 1, when administered to a subject, results in an increase of at least 15% superoxide dismutase (SOD) levels.

25. The composition according to claim 1, when administered to a subject, results in a reduction of at least 15% gamma-glutamyl transferase (GGT) levels.

26. The composition according to claim 1 wherein:
the *Andrographis paniculata* extract is enriched in livolides;
the *Momordica charantia* extract is enriched in bitters; and
the *Phyllanthus niruri* extract is enriched in tannins.

27. The composition according to claim 1 wherein:
the *Andrographis paniculata* extract is enriched in livolides;
the *Zingiber officinale* extract is enriched in zinzirols;
the *Brassica rapa* extract is enriched in turnitrates;
the *Momordica charantia* extract is enriched in bitters;
the *Asparagus racemosus* extract is enriched in saponins; and
the *Phyllanthus niruri* extract is enriched in tannins.

* * * * *